US012560588B2

(12) United States Patent
Chi et al.

(10) Patent No.: US 12,560,588 B2
(45) Date of Patent: Feb. 24, 2026

(54) HIGH-EFFICIENCY SCREENING METHOD FOR RNA-TARGETING DRUGS USING NANOPORES

(71) Applicant: KOREA RESEARCH INSTITUTE OF BIOSCIENCE AND BIOTECHNOLOGY, Daejeon (KR)

(72) Inventors: Seung-Wook Chi, Daejeon (KR); Mi-Kyung Lee, Daejeon (KR); Donghwa Lee, Daejeon (KR); Sohee Oh, Daejeon (KR)

(73) Assignee: KOREA RESEARCH INSTITUTE OF BIOSCIENCE AND BIOTECHNOLOGY, Daejeon (KR)

( * ) Notice: Subject to any disclaimer, the term of this patent is extended or adjusted under 35 U.S.C. 154(b) by 358 days.

(21) Appl. No.: 18/191,388

(22) Filed: Mar. 28, 2023

(65) Prior Publication Data

US 2023/0304989 A1 Sep. 28, 2023

Related U.S. Application Data

(63) Continuation-in-part of application No. PCT/KR2021/013103, filed on Sep. 27, 2021.

(30) Foreign Application Priority Data

Sep. 28, 2020 (KR) ........................ 10-2020-0126367

(51) Int. Cl.
*G01N 33/487* (2006.01)
*C12N 15/113* (2010.01)

(52) U.S. Cl.
CPC ..... *G01N 33/48721* (2013.01); *C12N 15/113* (2013.01); *C12N 2310/531* (2013.01)

(58) Field of Classification Search
CPC ........... G01N 33/48721; G01N 33/487; C12N 15/113; C12N 15/115; C12N 2310/531;
(Continued)

(56) References Cited

U.S. PATENT DOCUMENTS 10,006,905 B2 6/2018 Maglia et al.
10,514,378 B2 12/2019 Maglia et al.
(Continued)

FOREIGN PATENT DOCUMENTS

CN 105259229 B 4/2018
KR 10-2010-0017905 A 2/2010
(Continued)

OTHER PUBLICATIONS

Henley, Studying RNA sequence and structure using solid-state and hybrid biomimetic nanopores, PHD thesis of the College of Science of Northeastern University, 2017 (Year: 2017).*
(Continued)

*Primary Examiner* — Shizhi Qian
(74) *Attorney, Agent, or Firm* — Sughrue Mion, PLLC

(57) ABSTRACT

The disclosure relates to nanopore-based technology for screening of drugs against target RNA. According to the screening method of the disclosure, drugs targeting RNA can be efficiently screened even with a very small amount sample of picomolar concentration. The discovered drugs targeting RNA can be used in the treatment of diseases associated with RNAs.

9 Claims, 18 Drawing Sheets

Specification includes a Sequence Listing.

(58) Field of Classification Search
CPC ............ C12N 2310/16; C12N 2320/10; C12Q 1/6869
See application file for complete search history.

(56) References Cited

U.S. PATENT DOCUMENTS

| | | | | |
|---|---|---|---|---|
| 10,802,015 | B2 | 10/2020 | Maglia et al. | |
| 10,921,309 | B2 | 2/2021 | Movileanu et al. | |
| 10,976,311 | B2 | 4/2021 | Maglia et al. | |
| 11,474,093 | B2 | 10/2022 | Chi et al. | |
| 2010/0286082 | A1 | 11/2010 | Breaker et al. | |
| 2016/0032236 | A1* | 2/2016 | Nivala | C12Q 1/48 435/7.1 |
| 2016/0053300 | A1 | 2/2016 | Maglia et al. | |
| 2016/0370358 | A1 | 12/2016 | Maglia et al. | |
| 2018/0335425 | A1 | 11/2018 | Maglia et al. | |
| 2018/0364214 | A1* | 12/2018 | Maglia | C07K 14/001 |
| 2019/0128867 | A1 | 5/2019 | Movileanu et al. | |
| 2019/0162713 | A1 | 5/2019 | Chi et al. | |
| 2019/0346431 | A1 | 11/2019 | Maglia et al. | |
| 2020/0072824 | A1 | 3/2020 | Maglia et al. | |
| 2021/0405039 | A1 | 12/2021 | Maglia et al. | |

FOREIGN PATENT DOCUMENTS

| | | | |
|---|---|---|---|
| KR | 10-2017-0089471 | A | 8/2017 |
| KR | 10-2018-0108281 | A | 10/2018 |

OTHER PUBLICATIONS

Blount et al., Riboswitches as antibacterial drug targets, Nature biotechnology, 2006, 24(12), 1558-1564 (Year: 2006).*

Niedzwiecki et al., Sampling a biomarker of the Human Immunodeficiency Virus across a synthetic nanopore, ACS Nano, 2013, 7(4), 3341-3350 (Year: 2013).*

Clamer et al., Detection of 3'-End RNA Uridylation with a protein nanopore, ACS Nano, 2014, 8(2), 1364-1374 (Year: 2014).*

Dong-Hwa Lee et al., "Tertiary RNA Folding-Targeted Drug Screening Strategy Using a Protein Nanopore", Analytical Chemistry, 2021, vol. 93, pp. 2811-2819 (9 pages.

Bala Murali Venkatesan et al., "Nanopore sensors for nucleic acid analysis", Nature Nanotechnology, 2011, vol. 6, pp. 615-624 (10 pages).

Marion Kirchner et al., "An in vivo high-throughput screening for riboswitch ligands using a reverse reporter gene system", Scientific Reports, 2017, vol. 7, No. 7732, pp. 1-11 (11 pages).

Sohee Oh et al., "Single-Molecule-Based Detection of Conserved Influenza A Virus RNA Promoter Using a Protein Nanopore", ACS Sensors, 2019, vol. 4, pp. 2849-2853 (5 pages).

Meni Wanunu et al., "Nanopore Analysis of Individual RNA/Antibiotic Complexes", ACS Nano, 2011, vol. 5, No. 12, pp. 9345-9353 (9 pages).

Xinyue Zhang et al., "Nanopore electric snapshots of an RNA tertiary folding pathway", Nature Communications, 2017, vol. 8, No. 1458, pp. 1-11 (11 pages).

Carolyn Shasha et al., "Nanopore-Based Conformational Analysis of a Viral RNA Drug Target", ACS Nano, 2014, vol. 8, No. 6, pp. 6425-6430 (6 pages).

Piotr Machtel et al., "Emerging applications of riboswitches—from antibacterial targets to molecular tools", J Appl Genetics, 2016, vol. 57, pp. 531-541 (11 pages).

* cited by examiner

NC1

NC2

NC4

SEQUENCE LISTING

```
Sequence total quantity: 6
SEQ ID NO: 1            moltype = RNA  length = 71
FEATURE                 Location/Qualifiers
source                  1..71
                        mol_type = other RNA
                        organism = synthetic construct
SEQUENCE: 1
ggcttcatat aatcctaatg atatggtttg ggagtttcta ccaagagcct taaactcttg  60
attatgaagt c                                                        71

SEQ ID NO: 2            moltype = RNA  length = 71
FEATURE                 Location/Qualifiers
source                  1..71
                        mol_type = other RNA
                        organism = synthetic construct
SEQUENCE: 2
ggcttcatat aatccgaatg atatggtttc ggagcttcca ccaagagcct taaactcttg  60
attatgaagt c                                                        71

SEQ ID NO: 3            moltype = RNA  length = 82
FEATURE                 Location/Qualifiers
source                  1..82
                        mol_type = other RNA
                        organism = synthetic construct
SEQUENCE: 3
gcgactcggg gtgcccttct gcgtgaaggc tgagaaatac ccgtatcacc tgatctggat  60
aatgccagcg tagggaagtc gc                                            82

SEQ ID NO: 4            moltype = RNA  length = 55
FEATURE                 Location/Qualifiers
source                  1..55
                        mol_type = other RNA
                        organism = synthetic construct
SEQUENCE: 4
aaaaaaaaaa aaaaaaaaaa aaaaagtaga aacaaggctt cggcctgctt ttgct       55
```

-continued

```
SEQ ID NO: 5            moltype = RNA  length = 55
FEATURE                 Location/Qualifiers
source                  1..55
                        mol_type = other RNA
                        organism = synthetic construct
SEQUENCE: 5
agtagaaaca aggcttcggc ctgcttttgc tacacacaca cacacacaca cacac       55

SEQ ID NO: 6            moltype = RNA  length = 36
FEATURE                 Location/Qualifiers
source                  1..36
                        mol_type = other RNA
                        organism = synthetic construct
SEQUENCE: 6
ggagaggttc tagctacacc ctctataaaa aactaa                            36
```

HIGH-EFFICIENCY SCREENING METHOD FOR RNA-TARGETING DRUGS USING NANOPORES

CROSS REFERENCE TO RELATED APPLICATION

The present application is a continuation in part of PCT Application PCT/KR2021/013103 filed on Sep. 27, 2021, which claims priority to Korean Patent Application No. 10-2020-0126367, filed Sep. 28, 2020, the entire contents of which is incorporated herein for all purposes by this reference.

SEQUENCE LISTING

The content of the electronically submitted sequence listing, file name: Q286284 Sequence Listing as filed.TXT; size: 6,636 bytes; and date of creation: Mar. 28, 2023, is hereby incorporated by reference in their entirety.

BACKGROUND OF THE INVENTION

Field of the Invention

The disclosure relates to a high-efficiency screening method for RNA-targeting drugs using nanopores

Description of the Related Art

To date, most of the drugs, which account for 70 to 80% of the drugs, have used proteins, the last product of the genes, as target molecules. However, since it is known that ribonucleic acid(RNA) molecules, one of the products of genome, can be a target molecule of the drug, attention is drawn to an efficient screening method that can select compounds to be bound to RNA.

RNA is known as an intermediate product that expresses DNA information as a protein in the flow of genetic information. In particular, the untranslated region(UTR) of mRNA is known to have important information that determines the efficiency of the mRNA expressed as a protein, and the stability of the mRNA itself and the location of mRNA. The UTR structure of such mRNA mostly has a two-dimensional or three-dimensional structure, and is characterized in shape and sequences. In particular, since the three-dimensional structure shows its function through specific binding to RNA-bound protein in vivo, RNAs with specific structures can be an important target molecule within cells. For example, the 16s rRNA A site of the bacteria, the HIV virus's trans-activating region(TAR) binding site, the REV-response element(RRE) binding site, iron responsive element(IRE) mRNA, thymidylate synthetase mRNA, and the like are recognized as target molecules. In addition, the role of UTR of mRNA, such as various cytokines, substances that convey the perceptions and signals between cells, growth factors, and various spherical proteins, begins to identify, and its importance is recognized. Accordingly, the specific sequences and shape of mRNA are attractive RNA targets for drug discovery. In addition, the UTR of various mRNAs directly related to diseases has a specific shape and sequence, so it is important drug target.

Riboswitch controls the gene expression of bacteria by binding to ions and small molecule metabolites such as amino acids and their derivatives (lysine, glycine, SAM. SAH), coenzymes (FMN, TPP, coenzyme B12), nucleus and their derivatives (adenine, guanine, c-di-GMP, c-di-AMP, preQ1) and ions ($MG^{2+}$). The riboswitch consists of an aptamer domain and an expression platform domain. The binding of the aptamer domain of the riboswitch to its cognate metabolite induces tertiary folding, including sequential conformational changes in the expression platform domain. Through this structural rearrangement, the riboswitch regulates the transcription or translation of genes related to bacterial metabolism. The riboswitch has evolved to recognize small molecules with high selectivity, and is present in bacteria, not eukaryotic, so that only bacteria can be targeted without any cross-reactivity. Thus, targeting bacterial riboswitches can be a promising strategy to overcome antibiotic resistance, especially in superbacteria.

Despite the importance of disease-related RNAs as a therapeutic target, efficient drug screening of small molecule drugs on such RNAs is limited due to the need for a large amount of RNAs, the low sensitivity of the surface plasma resonance for the detection of small molecule drugs binding to RNAs, the necessity of the chemical labeling of RNAs in fluorescent-based analysis, or the like. Therefore, the development of new drug screening technologies with high efficiency will promote the discovery of drugs for various RNA-mediated diseases.

Nanopore sensing is a new technology for single molecule analysis of biomolecules. The translocation of analytes through a single nanopore channel at applied voltages induces a temporary blockade of ionic current, which is measured as a current amplitude and dwell time parameters. Since the first nanopore-detection of the homouridine RNA fragment (polyU), a variety of nanopore-based approaches have been used to detect nucleic acids. Among the protein nanopores, alpha-hemolysin(α-HL), a toxin secreted by *Staphylococcus aureus*, is mainly used for nucleic acid analysis. A protein monomer consisting of 293 amino acids is self-assembled in lipid bilayer to form a stable heptameric pore with a channel up to 10 nm in length. The α-HL nanopore is a suitable platform for the detection of single molecule, especially the detection of nucleic acids because of its precise geometry and narrow constriction with 1.4 nm diameter. However, protein nanopore-based analysis for small molecule drug screening against RNA targets is still limited.

Therefore, it is necessary to develop a technology that accurately and efficiently screens RNA-targeting small molecule drugs based on nanopores with a very small amount of sample.

SUMMARY OF THE INVENTION

One object of the disclosure is to provide a method for screening an RNA-targeting drug using nanopores.

Another object of the disclosure is to provide a kit and device for screening an RNA-targeting drug including nanopores.

Still another aspect of the disclosure provides an antibiotic composition comprising at least one selected from the group consisting of dicaffeoylquinic acid, luteolin-7-glucuronide, and salts thereof as an active ingredient.

DETAILED DESCRIPTION OF THE INVENTION

1. Screening Method of RNA-Targeting Drugs

Figure 1:
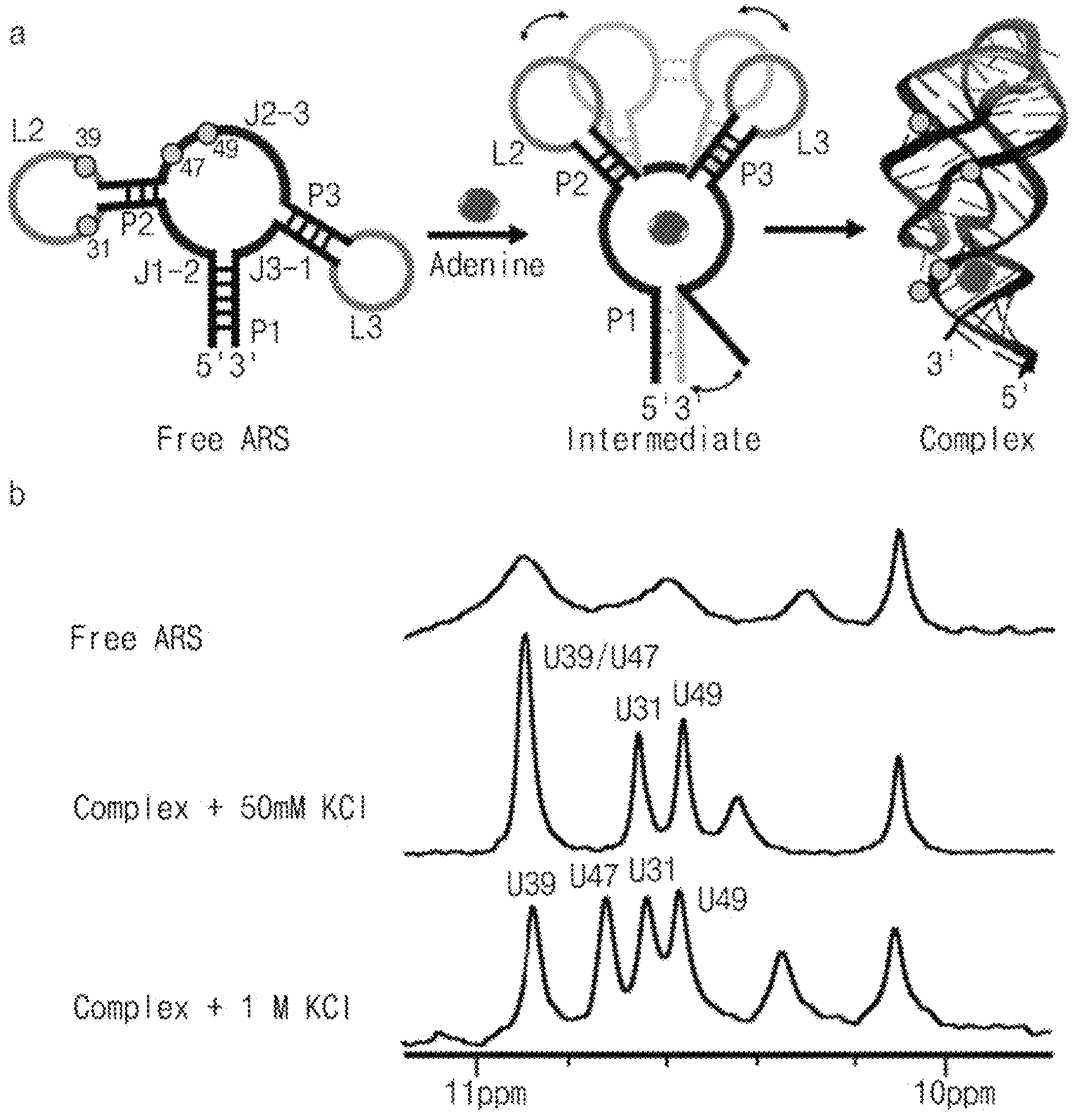
FIG. 1 shows NMR-based analysis of adenine-induced tertiary folding of ARS: (a) Three molecular states in the adenine-induced tertiary folding of ARS; (b) The 1D $^{1}H$ NMR spectra of free ARS and ARS-adenine complex in the presence of 50 mM KCl or 1 M KCl.

Hereinafter, the disclosure will be described in detail.

One aspect of the disclosure relates to a method for screening RNA-targeting drugs using nanopores.

The method for screening an RNA-targeting drug of the disclosure includes (a) measuring an electrical signal generated by a target RNA translocating a nanopore; (b) treating a candidate substance expected to bind to the target RNA with the target RNA, and measuring the electrical signal generated by the target RNA translocating the nanopore; and (c) comparing the electrical signals measured in the steps (a) and (b) and selecting the candidate substance as a drug to be bound to the target RNA when there is a change in the electrical signal.

The "nanopore" refers to a structure in which ions and/or charged molecules can translocate from one compartment to another compartment. The "nano" in the nanopore means a size less than about 1 μm and greater than about 0.1 nm. The diameter of the nanopore may be specifically about 0.5 nm to about 25 nm, about 0.5 nm to about 10 nm, about 0.5 nm to about 8 nm, about 0.5 nm to about 6 nm, about 0.5 nm to about 5 nm, about 1 nm to about 3 nm, or about 1.5 nm.

The nanopore may be a protein nanopore having a narrow constriction, for example, α-hemolysin, ClyA, aerolysin, lysenin, CsgG, FhuA, FraC, MspA, PlyAB, Phi29, PA63, OmpG, or the like. The α-hemolysin protein may include both wild type and variant. The α-hemolysin protein nanopore monomer forms a heptameric pore having a long and narrow β-barrel (having a length of about 10 nm and a diameter of about 1.4 nm) on a flat surface of lipid bilayer. The α-hemolysin protein nanopore may be connected to a voltage at both ends thereof to allow molecules to translocate from a first compartment to a second compartment, and may generate different electrical signals according to charge characteristics. Thus, α-hemolysin protein nanopore may be useful as a high sensitivity sensor for detecting biomolecules at a single molecule level.

The "target RNA" is an RNA associated with diseases, which may be an mRNA involved in the transcription control of the genes related to the diseases. In addition, the target RNA may itself form at least one stem-loop or triplex structure, and any RNA that has a specific two-dimensional or three-dimensional structure and whose two-dimensional structure is stabilized or whose three-dimensional structure is changed by binding to ligand may be included in the target RNA, without limitation. The target RNA may have, for example, a partial duplex structure. Alternatively, it may be a pseudoknot structure that forms a stem by forming a double helix from the loop portion of one stem-loop structure and another portion of RNA. In addition, the RNAs associated with diseases bear a stem-loop structure known to date. There are MicroRNAs (e.g., miR-21 and miR-96), and MALAT1 RNA is known as an anticancer target having a triplex structure. All of them are bound with drugs to induce a variety of structural changes, so they are promising targets for treating RNA-mediated diseases.

In specific embodiments, the target RNA may include a site that can regulate the gene expression for the survival of the bacteria, and may be all or part of the riboswitch derived from bacteria, and any RNA containing an aptamer domain capable of binding to a ligand may be included without limitation. For example, it may include nucleotide sequences represented by any one selected in the group consisting of SEQ ID NO: 1 to 3, and SEQ ID NO: 6.

The "riboswitch" refers to the regulatory site of mRNA to which a small molecule such as a specific metabolite in the cell can specifically bind, and the riboswitch plays a role of detection of the concentration of the specific metabolite and regulates the expression level of the gene encoded by downstream mRNA. That is, protein expression from this mRNA is controlled according to whether a specific substance (e.g., metabolite) is bound to the riboswitch. The riboswitch is divided into an aptamer domain and an expression platform domain. The aptamer domain is a site that directly binds to a specific substance, and the expression platform domain is a site where structural changes occur in response to changes in the aptamer domain. The aptamer domain of the riboswitch has a highly conserved consensus sequences and structure. The riboswitch may be, for example, purine riboswitch including adenine riboswitch and guanine riboswitch, lysine riboswitch, cyclic di-GMP riboswitch, glmS riboswitch, TPP riboswitch, FMN riboswitch, or the like.

In specific embodiments, the target RNA may be all or part of conserved sequences in viral RNAs, such as sequences of SEQ ID NO: 4 or SEQ ID NO: 5. Specifically, the conserved sequences may be a promoter sequences and is highly conserved in various variants of epidemic virus, so it is possible to screen drugs that initiates or regulates the transcription by targeting the conserved sequences.

The "RNA-targeting drug" means a drug that targets RNA, and may include, without limitation, any drug that inhibits the function of target RNA by specifically binding to the target RNA and causes a two-dimensional or three-dimensional structural change of the target RNA. For example, it may be any one molecule selected from the group consisting of nucleic acid, protein, peptides, and compounds.

The RNA-targeting drug is to treat RNA-mediated diseases by regulating the transcription of the target RNA, and may be involved in the treatment of multiple RNA-mediated diseases including microbial infections, cancer, metabolic diseases, degenerative diseases, cardiovascular diseases, lung diseases, immune diseases. For example, a drug targeting Malat1 RNA, known as an anticancer target, may be involved in the treatment of cancer. Thus, the RNA-targeting drug may be an anticancer agent, a metabolic disease treatment, a degenerative disease treatment, a cardiovascular disease treatment, a lung disease treatment, an immune disease treatment, an antibacterial agent, an antibiotic agent, or an antiviral agent.

In specific embodiments, the drug that binds to the RNA target may be a small molecule that can be bound to the aptamer region of bacterial riboswitch. The transcription and translation functions of the small molecule may be regulated by binding to a target riboswitch, and the small molecule may be a ligand that targets the riboswitch found in bacteria, for example. Ligands that bind to the riboswitch in the resistant strain of antibiotics may be a new antibiotic candidate that can overcome the resistance of antibiotics.

In specific embodiments, the RNA-targeting drug may be a small molecule that binds to the conserved sequences of RNA virus. The small molecule may bind to the promoter of the RNA virus so that the transcription and translation function of the small molecule is regulated, thereby treating the RNA-mediated diseases.

In the disclosure, the term, "candidate substance" means all substances that are expected to bind to target RNA. For example, any molecules such as small molecules, proteins, oligopeptides, polysaccharides, polynucleotides, or the like may be the candidate substance. The candidate substance includes not only natural substance but also synthetic substance.

In the disclosure, the "RNA-ligand complex" or "RNA-drug complex" means a complex formed by binding of the target RNA and ligand or target drug thereof, and in the specification, the "RNA-ligand complex" and "RNA-drug complex" are used interactively in an equal sense, and may include any one that has a charge without restrictions on the method or location of the binding, the size of the complex, etc. in forming the complex.

In the disclosure, since the RNA-drug complex shows a characteristic nanopore event form having a single or double current blockades and substantially increased dwell time, it was confirmed that it was possible detect the drugs that bind to the target RNA by analyzing such a nanopore event. Thus, the screening method of the RNA-targeting drug of the disclosure can be useful for screening drugs that target the RNA associated with disease.

The "electrical signal" refers to a signal that is generated when the flow of ions is obstructed as ions and/or charged small molecules translocate from one compartment to another compartment separated from the one compartment by a membrane, for example, from a first compartment to a second compartment. Particularly, the electric signal may be specifically open pore current ($I_0$), a magnitude of current drop ($\Delta I$), dwell time, nanopore event conformation, or the like. The open pore current is a state in which analyte does not exist and only the nanopore is present, which means a basic level.

The "magnitude of current drop ($\Delta I$)" may also be referred to as current blockade through nanopores, and specifically, the "magnitude of current drop ($\Delta I = I - I_0$)" refers to a difference between the current blockade (I) for analyte and the current blockade ($I_0$) for pore current.

The "dwell time" refers to the time where the analyte takes to translocate through the nanopore, or the time to stay in the entrance of the nanopore and/or inside the nanopore.

The "nanopore event conformation" refers to the confirmation of a current peak that the analyte translocates the nanopore, for example, may be expressed in a form of a peak, a rate of peaks, or a combination thereof.

The "screening" refers to a process of extracting, separating, and confirming a compound having a preferred sensitivity or activity among the samples or candidate substances in the fewest possible steps, and it is for the purpose of discovering the drug that binds to the target RNA specifically.

The method for screening a drug binding to the target RNA may be to detect the presence of the RNA-drug complex formed by binding of the target RNA and the drug.

The detection of the RNA-drug complex may be to detect dynamic changes including two-dimensional or three-dimensional structural changes and/or temporary structural changes of the RNA, that occurs in response to the binding of the drug to the target RNA by measuring and comparing an electrical signal. Specifically, it may be determined that the RNA-drug complex is formed in a case that a change in the electrical signal is occurred before and after the reaction of the target RNA and the candidate substance.

The "case that a change in electrical signal is occurred" refers to a case where the dwell time and/or nanopore event conformation before and after the reaction of the target RNA and the candidate substance are changed. Particularly, it may refer to an increase in nanopore dwell time after treatment of a candidate substance, or a new nanopore event conformation appearing after treatment of a candidate substance, or a change in the rates of two or more types of events before and after treatment of a candidate substance. Particularly, the increase in dwell time may be 1.1 times or more, 1.3 times or more, 1.5 times or more, 1.8 times or more, 2 times or more, 3 times or more, 5 times or more, or 8 times or more compared to before the reaction. The appearance of a new nanopore event conformation may be that the single-level electrical signal is changed to a dual-level electrical signal after the candidate substance is treated. The change in the rates of the two or more types of events may be that the frequency or rate thereof of the two types of events may change before and after the treatment of the candidate substance. Specifically, it may be a change in the frequency or rate thereof of multiple current level signals compared to a single current level signal generated within the unit time.

In the screening method of the disclosure, if the candidate substance is a drug that binds to the target RNA, the candidate substance is bound to the target RNA to form an RNA-drug complex, and the RNA-drug complex is structurally stabilized and does not translocate the nanopore immediately and is captured in the nanopore lumen. After captured, it will take time for the RNA-drug complex to be unzipped, so the time for staying in the nanopore will be longer, so the dwell time before and after the reaction of the candidate substance with the target RNA is measured. When the dwell time after reaction increases, it can be determined that the candidate substance is the drug that specifically binds to the target RNA.

In addition, in the screening method of the disclosure, if the candidate substance is a drug that binds to the target RNA, the candidate substance binds to the target RNA to form an RNA-drug complex, and the RNA-drug complex does not translocate the nanopore immediately and is captured in the nanopore lumen. After captured, the RNA-drug complex is unzipped so that the structure is changed. The current level is generated according to the change of such a structure, so the electrical signals before and after the treatment of the candidate substance to the target RNA are measured. If new type event conformation is occurred after the reaction, it may determine that the candidate substance is the drug that specifically binds to the target RNA.

Figure 2:
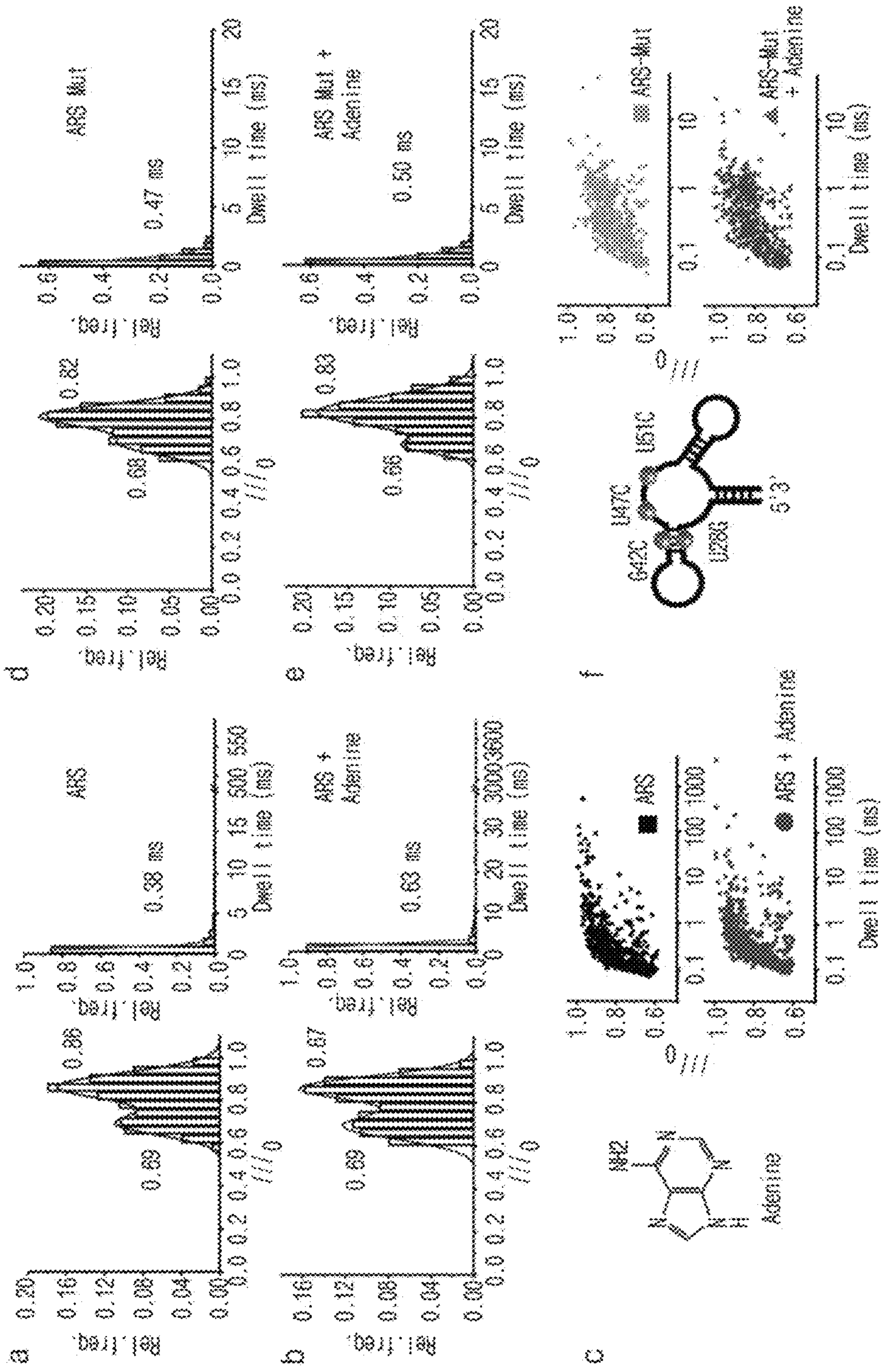
FIG. 2 shows statistical analysis results for nanopore events of ARS and ARS-Mut with ligands: (a) in FIG. 2 is a histogram of current drop ($I/I_0$) and dwell time ($t_d$) for free ARS; (b) in FIG. 2 is a histogram of current drop ($I/I_0$) and dwell time ($t_d$) for ARS-adenine complex; (c) in FIG. 2 shows a structure of adenine and a scatter plot of free ARS and adenine bound ARS; (d) in FIG. 2 is a histogram of current drop ($I/I_0$) and dwell time ($t_d$) for free ARS-Mut; (e) in FIG. 2 is a histogram of current drop ($I/I_0$) and dwell time ($t_d$) for adenine bound ARS-Mut; (f) in FIG. 2 shows a structure of ARS-Mut with four base mutations (U28G, G42C, U47C and U51C) and a scatter plot of nanopore events for free ARS-Mut and adenine bound ARS-Mut.
Figure 3:
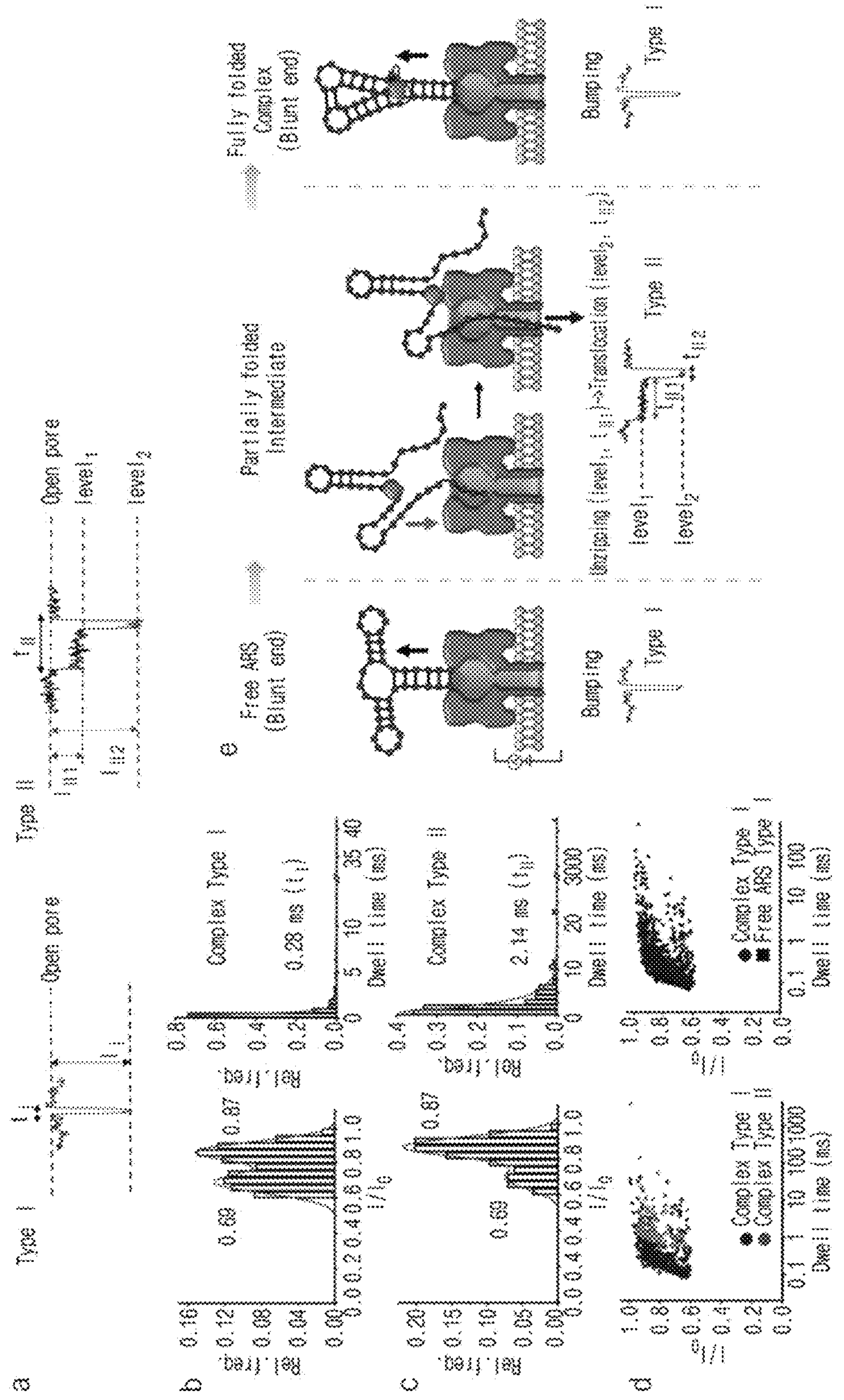
FIG. 3 shows statistical analysis results for nanopore events of ARS-adenine complex: (a) in FIG. 3 shows two types of current trace for ARS-adenine complex; (b) in FIG. 3 shows a histogram of $I/I_0$ and dwell time of a type-I event; (c) in FIG. 3 is a histogram of $I/I_0$ and dwell time of a type-II event; (d) in FIG. 3 shows scatter plots of type I and type-II events for complex and free ARS; (e) in FIG. 3 shows a molecular model proposed for bumping or translocation of free ARS, intermediate and complex.
Figure 17:
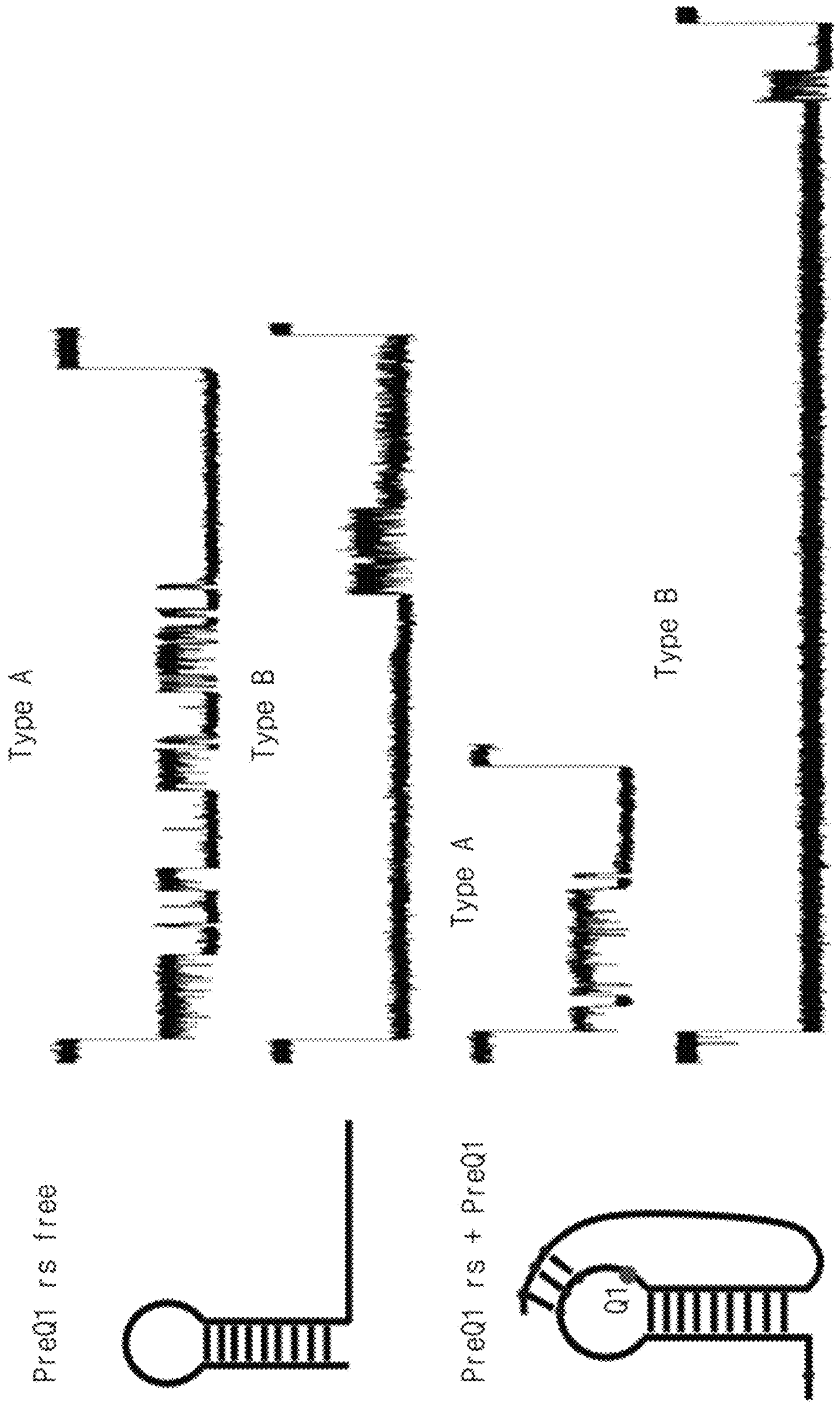
FIG. 17 shows a representative event shown in a α-hemolysin nanopore channel, and shows type A and type B events that appear in free preQ1-sensing riboswitch and ligand bound complex (preQ1 rs+preQ1). The type A and type B events are long-lived translocation events that appear specifically in the measurement of the preQ1-sensing riboswitch through nanopores.
Figure 18:
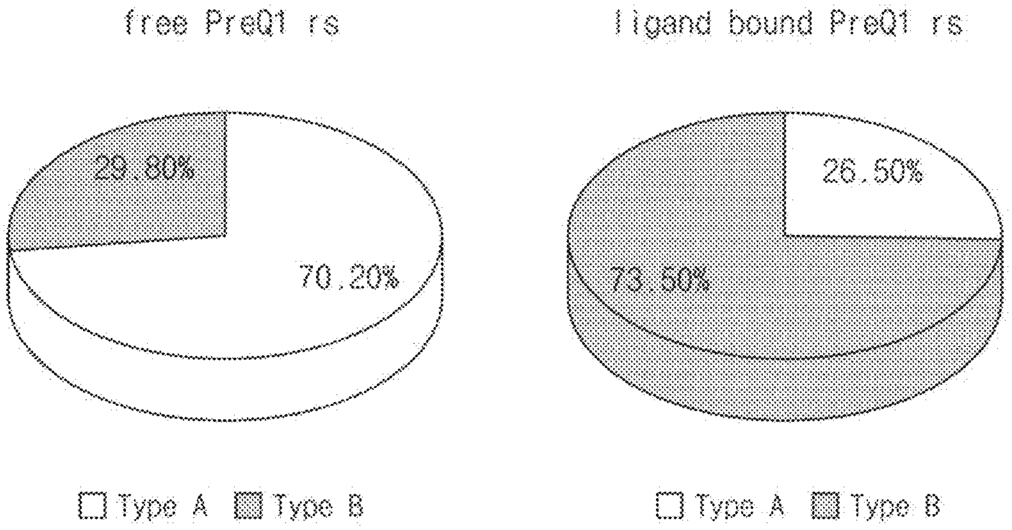
FIG. 18 shows a percentage of the type A and type B events that appear in free preQ1-sensing riboswitch and ligand bound preQ1-sensing riboswitch.

In one embodiment of the disclosure, when the RNA derived from the bacteria is present as free RNA, only a single-stage type-I event conformation was appeared, but when RNA exists in the RNA-drug complex, the type-I event as well as type-II event conformation with a two-stage current level appears together. Even in the case of nanopore dwell time, it was confirmed that the nanopore dwell time of the RNA-drug complex is more than 2 times higher than that of free RNA. Accordingly, it was confirmed that it is possible to discover drugs that target specific RNAs by using the nanopore and the specific RNA (FIGS. 2 and 3). In addition, when the RNA derived from the bacteria is free state, it was confirmed that the rate of the type A event was higher than the rate of the type B event, but when the RNA exists in the RNA-drug complex, the rate of the type B event is higher than the rate of the type A event, and the rate of type B event in the RNA-drug complex is about 1.5 times higher than the rate of type B event in the free RNA. Accordingly, it was confirmed that it is possible to discover drugs that targets specific RNAs using the nanopore and the target RNA (FIGS. 17 and 18).

Figure 13:
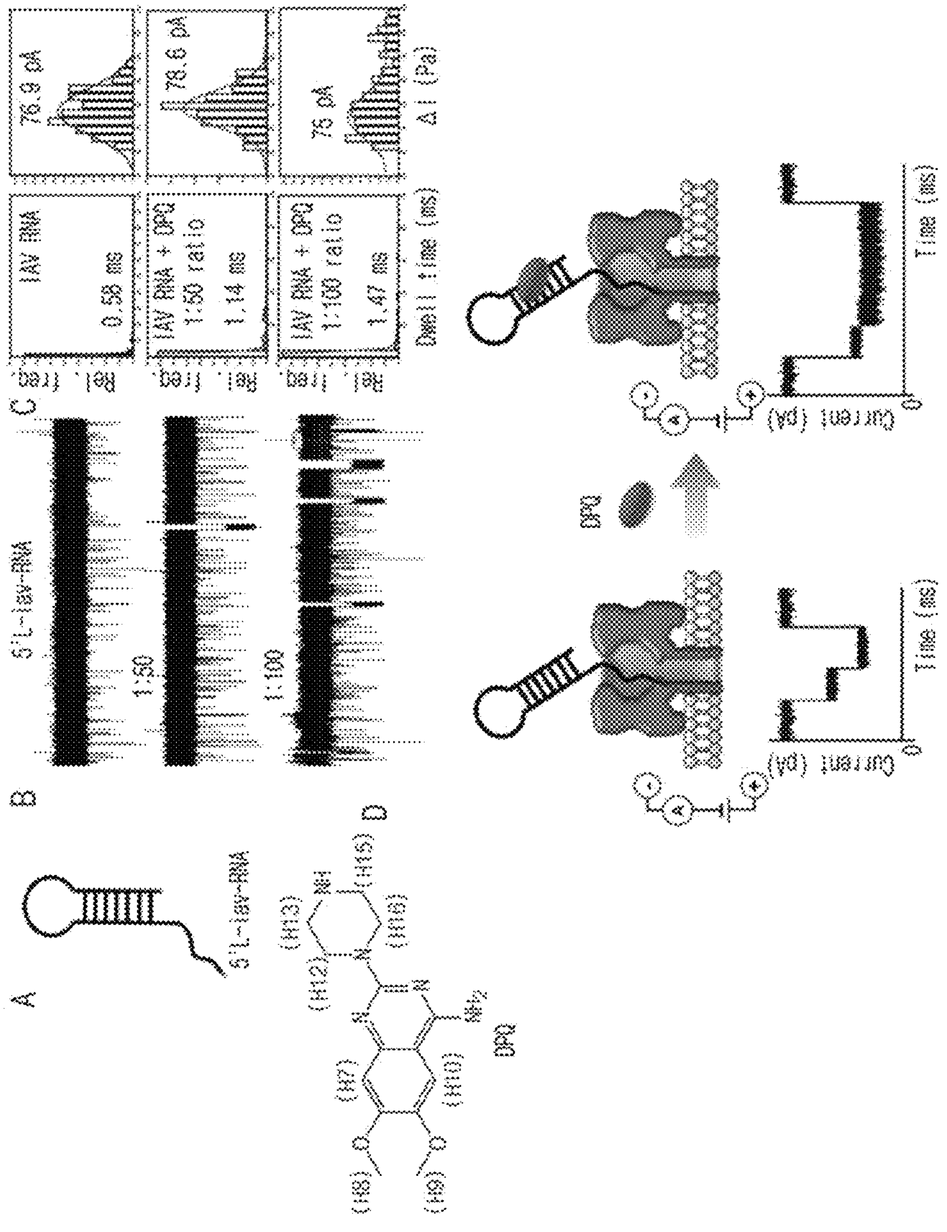
FIG. 13 shows a detection method of nanopore-based RNA-drug complex for IAV RNA using 5' end leader sequence: (a) shows two-dimensional structure of IAV RNA having 5' end leader sequence and 6,7-dimethoxy-2-(1-piperazinyl)-4-quinazolinamine(DPQ), (b) shows the detection of IAV RNA using DPQ bound to IAV RNA having 5' end leader sequences at 100 mV, (c) shows a histogram of dwell time and current trace for the increased binding rates of free 5'L-iav-RNA and the 5'L-iav-RNA/DPQ complex, and (d) shows a molecular diagram for the detection of IAV RNA and the DPQ complex.
Figure 14:
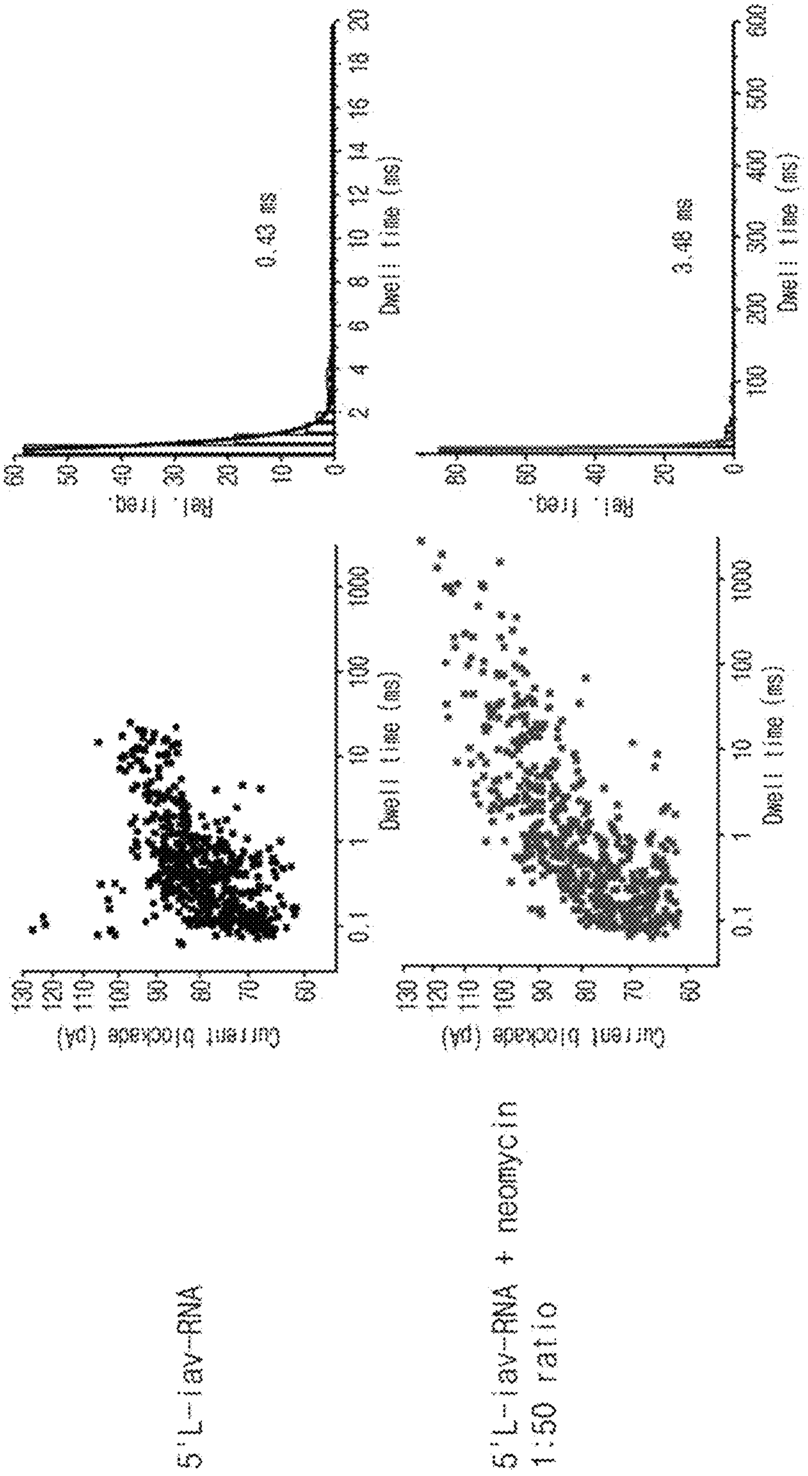
FIG. 14 shows a detection method of neomycin bound to 5'L-iav-RNA using nanopore: scatter plot and histogram of dwell time for free 5'L-iav-RNA and 5'L-iav-RNA/neomycin complex (ratio of 1:50).

In another embodiment of the disclosure, it was confirmed that the nanopore dwell time of viral RNA-drug complex is increased by about 2 to 8 times compared to that of free viral RNA, depending on the type and concentration of the drug. Accordingly, it was confirmed that it is possible to discover drugs targeting specific RNAs using the nanopore (FIGS. 13 and 14).

In another aspect, the disclosure relates to a method for screening for an antimicrobial drugs, antibiotics or antiviral agent using nanopores.

A method for screening an antibacterial, antibiotic or antiviral agent of the disclosure includes (a) measuring an electrical signal generated by a target RNA translocating a nanopore; (b) treating a candidate substance expected to bind to the target RNA with the target RNA, and measuring the electrical signal generated by the target RNA translocating the nanopore; and (c) comparing the electrical signals measured in the steps (a) and (b) and selecting the candidate substance as riboswitch-targeting substance when there is a change in the electrical signal.

In the disclosure, the terms, "target RNA", "RNA-targeting drug", "candidate substance", "nanopore", "electrical signal" and "screening" are as described above.

In one embodiment of the disclosure, 40 candidate substances were primarily selected from 766 natural products libraries through in silico screening, and nanopore-based drug screening for them was conducted. As a result, three groups in which more than 10% type-II translocation event was observed were selected. Since then, three new RNA-targeting drugs have been discovered through individual nanopore screening, and it was confirmed that the discovered 3,4-dicaffeoylquinic acid, 4,5-dicaffeoylquinic acid and luteolin-7-glucuronide all showed type-II translocation event and duel-level signal, and the nanopore dwell time more than twice as large as the nanopore dwell time in free RNA.

2. Kit and Device for Screening RNA-Targeting Drugs

In another aspect, the disclosure provides a kit for screening an RNA-targeting drug including (i) nanopore, (ii) target RNA, and (iii) a configuration for measuring ion current and dwell time.

In the disclosure, the terms, "target RNA", "RNA-targeting drug", "candidate substance", "nanopore", "electrical signal" and "screening" are as described above.

The kit for screening an RNA-targeting drug of the disclosure may provide a space in which the nanopores exist is divided into two compartments (e.g., a first compartment and a second compartment, or a cis compartment and a trans compartment) by a membrane containing nanopores. Also, any one of the two compartments can be provided in a state containing the target RNA. When a candidate substance expected to bind to a target RNA is supplied into the compartment containing the target RNA of the kit for screening an RNA-targeting drug of the disclosure, the candidate substance is bound to the target RNA to form RNA-drug complex, and the RNA-drug complex will not translocate the nanopore immediately, and is captured in the nanopore lumen. After captured, it will take a time for the RNA-drug complex to be unzipped and the time to stay in the nanopores will be longer. By measuring the nanopore dwell time before and after reacting the candidate substance with the target RNA, when the dwell time increases after the reaction, it can determine that the candidate substance is the drug that specifically binds to the target RNA. In addition, if the RNA-drug complex captured into the nanopore, structural changes of the RNA-drug complex will occur due to the unzipping and then generates significant changes in the current level. If the electrical signals before and after treating the candidate substance to the target RNA are measured and the new type of event confirmation appears after the reaction, it can determine that the candidate substance is the drug that specifically binds to the target RNA. That is, if the candidate substances specifically binds to the target RNA, the electrical signals change before and after the treatment of the candidate substance, and if the candidate substance does not specifically bind to the target RNA, the electrical signal does not change before and after the treatment of the candidate substance, so that it is possible to screen the drug that specifically binds to the target RNA.

The kit for screening an RNA-targeting drug of the disclosure may be additionally provided with a configuration that can measure ion current, a magnitude of current drop, three-dimensional event conformation, or event duration.

In another aspect, the disclosure provides a nanopore device for screening an RNA-targeting drug including a chamber; a nanopore-containing membrane; and an electrode for applying a nanopore voltage, wherein a space in the chamber is divided into two compartments by the nanopore-containing membrane, and one compartment in the chamber includes a target RNA.

In the disclosure, the terms, "target RNA", "RNA-targeting drug", "candidate substance", "nanopore", "electrical signal" and "screening" are as described above.

The device of the disclosure includes a chamber; a nanopore-containing membrane; and an electrode for applying a voltage to the nanopore.

The chamber refers to a structure in which an inner space is formed to accommodate a certain volume fluid. The inner space of the chamber may be provided in a state in which the nanopore-containing space is divided into two compartment (e.g., first and second compartments, or cis compartment and trans compartment) by the nanopore-containing membrane. Also, any one of the two compartments in a state containing the target RNA may be provided.

Any membrane that can divide the space or chamber in which the nanopores exist into two compartments while serving as a support to which the nanopores can be fixed, can be included without limitation. The membrane serves to block the translocation of the fluid or substance contained in the fluid without additional means.

The device may include a liquid medium, and the liquid medium may be a solution containing salt. The ion current can flow when the salts translocate the nanopore between the two compartments divided by an insulating membrane. Any membrane that can divide the space or chamber in which the nanopores exist into two compartments while serving as a support to which the nanopores can be fixed may be included without restrictions. The membrane has a role in blocking the substance contained in the fluid or fluid unless any additional means is provided.

The device for screening an RNA-targeting drug of the disclosure may be further provided with a configuration that can measure the ion current, the magnitude of current drop, the three-dimensional event conformation, or the event duration when the electric field is applied through the electrode in the chamber or in the liquid medium in the chamber.

The operation principle of the nanopore device for screening an RNA-targeting drug is the same as described in the method for screening an RNA-targeting drug and the kit for screening an RNA-targeting drug.

3. Antibiotic Composition

In another aspect, the disclosure provides an antibiotic composition comprising at least one selected from the group consisting of dicaffeoylquinic acid, luteolin-7-glucuronide, and salts thereof as an active ingredient The dicaffeoylquinic acid is an ester consisting of quinic acid and two caffeic acids, and quinic acid or derivatives thereof containing two or more caffeoyl groups is phytochemical separated from natural products, and is safe because it does not cause irritation to the human body.

The dicaffeoylquinic acid may have a general formula of Formula 1 below.

[Formula 1]

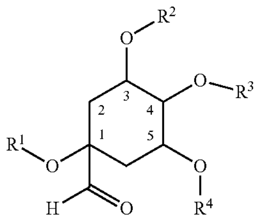

In Formula 1, $R^1$, $R^2$, $R^3$ and $R^4$ may be independently of hydrogen or caffeoyl. In particular, the $R^1$, $R^2$, $R^3$ and $R^4$ may include at least one hydrogen, especially two or more hydrogen. Specifically, the dicaffeoylquinic acid may be 1,3-dicaffeoylquinic acid, 1,4-dicaffeoylquinic acid, 1,5-dicaffeoylquinic acid, 3,4-dicaffeoylquinic acid, 3,5-dicaffeoylquinic acid, 4,5-dicaffeoylquinic acid, and especially 3,4-dicaffeoylquinic acid with the chemical structure of Formula 2 or 4,5-dicaffeoylquinic acid with the chemical structure of Formula 3.

[Formula 2]

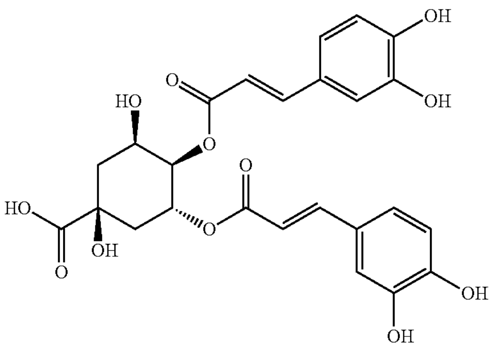

[Formula 3]

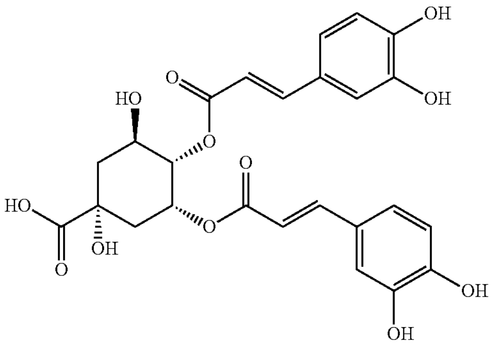

The luteolin-7-glucuronide is one of the flavonoid compounds, which may be a compound having a structure of Formula 4 below.

[Formula 4]

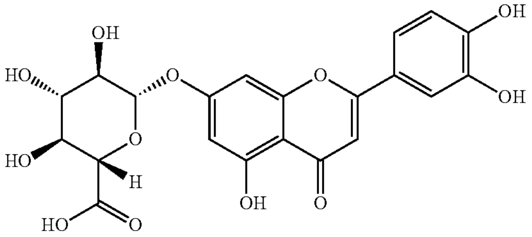

The salt may be a pharmaceutically acceptable salt, and refers to a salt of a compound that is pharmaceutically acceptable and that possesses the desired biological or pharmacological activity of the parent compound. Examples of such salts are not limited to this, but include acid addition salts formed with inorganic acids (e.g., hydrochloric acid, hydrobromic acid, sulfuric acid, phosphoric acid, nitric acid, and the like), and salts formed with organic acids such as acetic acid, oxalic acid, tartan acid, succinic acid, malic acid, fumaric acid, maleic acid, ascorbic acid, trifluoroacetic acid, benzoic acid, tannic acid, pamoic acid, alginic acid, polyglutamineic acid, naphthalene sulfonic acid, naphthalene disulfonic acid, and poly-galacturonic acid. The compounds may also be administered as pharmaceutically acceptable quaternary salts known by a person skilled in the art, which specifically includes chloride, bromide, iodide, —O-alkyl, toluenesulfonate, methylsulfonate, sulfonate, phosphate, or carboxylate (e.g., benzoate, succinate, acetate, glycolate, maleate, malate, fumarate, citrate, tartrate, ascorbate, cinnamoate, mandeloate and diphenylacetate). The compound of the Formula of the disclosure may include not only pharmaceutically acceptable salts, but also all salt, hydrates and solvents thereof that can be prepared by commonly employed methods.

The compounds of the disclosure have antibacterial effects for microorganisms having an adenine-sensing riboswitch. The compounds of the disclosure inhibit the growth or survival of microorganisms by binding to the adenine-sensing riboswitch essential for the survival of microorganisms. Thus, the compounds of the disclosure can be used as an active ingredient of the antibiotics composition that inhibits the growth or survival of microorganisms.

The adenine-sensing riboswitch(ARS) regulates the translation of adenosine deaminase(ADD), which is essential for bacterial purine metabolism. The adenine-sensing riboswitch is a biomic sensor that detects the concentration of adenine and regulates the expression amount of genes coded by downstream mRNA, and includes at least one stem-loop structure. For example, the aptamer domain of ARS of *Vibrio vulnificus* consists of three spiral stems (P1 to P3), two hairpin loops L2 and L3, and three binding sites (J1-2, J3-1, and J2-3) ((a) in FIG. 1). The ARS in free state is flexible, but is folds into a tertiary structure like a tuning-fork by its binding to ligands. Through the intermediate state, the tertiary structure of the complex is stabilized through the formation of a new base triplex of the adenine binding site and the hydrogen bond between the loops L2 and L3, and blocks the translation initiation site to stop protein synthesis. The ARS controls the translation of bacterial purine metabolism.

The antibiotic composition of the disclosure targets the bacterial riboswitch in bacteria, not eukaryotic, so that only bacteria can be suppressed by specifying only bacteria without cross reactions. Thus, the antibiotic composition of the disclosure may have an excellent antibacterial effect on superbacteria resistant to conventional antibiotics.

In one embodiment of the disclosure, through the screening method of the adenine-sensing riboswitch (ARS)-targeting drug, it was confirmed that 3,4-dicaffeoylquinic acid, 4,5-dicaffeoylquinic acid, and luteolin-7-glucuronide were bound to the adenine-sensing riboswitch to cause structural changes. From this, it can be seen that 3,4-dicaffeoylquinic acid, 4,5-dicaffeoylquinic acid, and luteolin-7-glucuronide can act as an antibiotic agent for microorganisms with the ARS.

The pharmaceutical composition may further include an active ingredient exhibiting antibacterial activity or antibiotics commonly used, in addition to the above compounds.

The pharmaceutical composition may further include a pharmaceutically acceptable carrier or additives in addition to the above active ingredient.

The 'pharmaceutically acceptable' means that a target to be applied (prescribed) has no toxicity more than adaptable without inhibiting the activity of an active ingredient. The 'carrier' is defined as a compound that facilitates the addition of a compound into cells or tissues.

The pharmaceutical composition may be administered in combination with any convenient carrier and the like, and such dosage forms may be single dosage or repeated dosage forms. The pharmaceutical composition may be a solid formulation or a liquid formulation. The solid formulation includes powders, granules, tablets, capsules, suppositories, and the like, but is not limited thereto. The solid formulation may include a carrier, a flavoring agent, a binder, a preservative, a disintegrant, a lubricant, a filler, etc., but is not limited thereto. The liquid formulation includes solutions such as water and a propylene glycol solution, suspensions, emulsions, and the like, but is not limited thereto and may be prepared by adding suitable coloring agents, flavoring agents, stabilizers, viscous agents, etc. For example, the powders may be prepared by simply mixing the above compound and a suitable pharmaceutically acceptable carrier such as lactose, starch, and microcrystalline cellulose. The granules may be prepared by mixing the above active ingredient, a suitable pharmaceutically acceptable carrier, and a suitable pharmaceutically acceptable binder such as polyvinylpyrrolidone and hydroxypropylcellulose, and then using a wet granulation method using a solvent such as water, ethanol, and isopropanol or a dry granulation method using a compressive force. Further, the tablets may be prepared by mixing the granules with a suitable pharmaceutically acceptable lubricant such as magnesium stearate, and then tableting the mixture using a tablet machine. When formulating the pharmaceutical composition in an injection, it can be prepared according to a commonly employed method for preparing an injection known in the art. When formulated as an injection, the composition may be in the form dispersed in a sterilized medium, such that the injection may be used as it is when administered to a patient, or may be in the form which is dispersed to be at a suitable concentration through the addition of distilled water for injection at the time of administration thereof.

The pharmaceutical composition may be administered with an injection (e.g., intravenous injection, intramuscular injection, intraperitoneal injection, infusion, subcutaneous injection, implant), an inhalant, an oral agent, a nasal injection, a vaginal agent, a rectal agent, a sublingual agent, a transdermal agent, a topical agent, or the like according to a disease to be treated and a condition of a subject, but is not limited thereto. Depending on a route of administration, the pharmaceutical composition may be formulated into a suitable dosage unit form including a pharmaceutically acceptable carrier, an additive, and a vehicle, which are commonly used and non-toxic.

The pharmaceutical composition may be administered at a daily dose of about 0.0001 mg/kg to about 10 g/kg, or at a daily dose of about 0.001 mg/kg to about 1 g/kg. The treatment-effective amount and effective dose of the pharmaceutical composition may be varied by the formulation method of the pharmaceutical composition, the administration mode, the administration time and/or the route of administration, and the type and extent of the reaction to be achieved by various factors such as the administration of the pharmaceutical composition, the type of the subject to be administered, the age, weight, general health condition, the symptom or severity of the disease, sex, diet, excretion, the components of the drug or other composition used concurrently or separately with the subject and similar factors well known in the pharmaceutical field, and those skilled in the art can easily determine and prescribe a dose effective for the desired treatment. In addition, if needed, the total daily dose may be administered portionwise for one day for convenience. The term "treatment-effective amount" means an amount sufficient to produce desired effects, including alleviation of condition that is indicative of the patient's bacterial disease (e.g., one or more symptoms) or resistance to conventional antibiotics in a patient with a bacterial disease, delay of disease progression, and the like.

According to the screening method of the disclosure, even with a very small amount of sample, a drug that targets a particular RNA can be effectively screened. The discovered RNA-targeting drug can be used for the treatment of diseases regulated by certain RNA.

The effect of the disclosure is not limited to the effect mentioned above, and other effects that are not mentioned can be clearly understood to those skilled in the art from the following descriptions.

Best Mode

Hereinafter, the disclosure will be described in detail by Examples and Experimental Examples. However, the following Examples and Experimental Examples are only for illustrating the disclosure, but are not limited by the following Examples and Experimental Examples.

Example 1

Class I RNA Target: Riboswitch with Long P1 Stem

<1-1>. Preparation of ARS RNA and Protein Nanopores

RNAs were synthesized by Integrated DNA Technologies (Coralville, IA, USA). The sequences information was shown in Table 1 below. All RNAs were dialyzed against 10 mM potassium phosphate (pH 6.2) buffer for at least 12 hours. After heating RNAs at 95° C. for 5 minutes, it was cooled quickly in the ice and annealed. The nanopore experiment was performed at RNA concentration of 10 to 500 nm. α-hemolysin (α-HL) protein was purchased from List Biological Laboratories Inc. (CAMPBELL, CA, USA). 1,2-diphytanoylsn-glycero-3-phosphocholine(DPhPC) was purchased from Avanti Polar Lipids (Alabaster, Al, USA).

TABLE 1

| Name | sequences (5'→3') | Length | SEQ ID NO |
|---|---|---|---|
| ARS | GGC UUC AUA UAA UCC UAA UGA UAU GGU UUG GGA GUU UCU ACC AAG AGC CUU AAA CUC UUG AUU AUG AAG UC | 71 nt | 1 |
| ARS-Mut | GGC UUC AUA UAA UCC GAA UGA UAU GGU UUC GGA GCU UCC ACC AAG AGC CUU AAA CUC UUG AUU AUG AAG UC | 71 nt | 2 |

<1-2>. Confirmation of Structural Changes of ARS Induced by Ligand

First, it was confirmed that the structure of riboswitch changed in three-dimension as ligands were bound to riboswitch using adenine-sensing riboswitch (ARS) and adenine through NMR analysis.

The ARS regulates the translation of adenosine deaminase (ADD), which is essential for bacterial purine metabolism. The aptamer domain of ARS *of Vibrio vulnificus* consists of three helical stems (P1 to P3), two hairpin loops (L2 and L3) and three binding sites (J1-2, J3-1 and J2-3) ((a) in FIG. 1). The ARS is flexible in a free state, but it is folded into a tertiary structure like a tuning-fork when bound to adenine. Through the intermediate state, the tertiary structure of the complex is stabilized through a new base triplex formation of the adenine binding site and the hydrogen bond between the loops L2 and L3 ((a) in FIG. 1). The ARS controls the translation of bacterial purine metabolism.

Specifically, 1D NMR test was performed with the ARS in the absence or presence of adenine in order to monitor the tertiary folding of the ARS induced by binding to the adenine. The ARS-adenine complex showed four characteristic imino proton peaks of U31, U39, U47, and U49 generated by a new hydrogen binding formation while the ARS was folded in three-dimension. The irregular basis pairs of U31 to U39 were formed when binding to the adenine, which is important for long distance tertiary interactions between loops L2 and L3 (FIG. 1). In addition, a new hydrogen was added. The binding network of the adenine binding site generated the U47 and U49 imago proton peaks. NMR analysis showed that the binding of the adenine to the ARS induced dramatic structural rearrangement and substantially stabilized the tertiary structure of the complex. Prior to the measurement of nanopore, it was confirmed that the ARS bound to the adenine at a high salt concentration (1M KCl) by detecting the four characteristic imino proton peaks of the complex ((b) in FIG. 1).

<1-3>. Confirmation of Detectability of ARS Structural Change using Nanopore

The α-hemolysin(α-HL) nanopore was used to confirm the interaction of riboswitch and ligands at a single molecule level.

Specifically, in the buffer containing 10 mM potassium phosphate (pH 6.2), 2 mM $MgCl_2$ and 1M KCl, free ARS or ARS-adenine complex was added to the cis face of a lipid bilayer with a single α-HL nanopore. If the voltage of (+) 100 mV is applied on the nanopore, the free ARS or the ARS-adenine complex is driven by electrophoresis to block the ion current. The nanopore events of the free ARS and ARS-adenine complex were statistically analyzed (a to c in FIG. 2). The nanopore event of the free ARS showed two average current blockades ($I/I_0$) of 0.69 and 0.86 at an average dwell time ($t_d$) of 0.38 ms (a in FIG. 2). In particular, the ARS-adenine complex produced the current blockade with the $I/I_0$ value (0.69 and 0.87) and an average $t_d$ (0.63 ms), which was significantly increased compared to the free ARS (b in FIG. 2).

Next, the nanopore event of the ARS mutant (ARS-Mut) with four base mutations (U28G, G42C, U47C and U51C) was measured as a negative control ((d) to (f) in FIG. 2). The values of $I/I_0$ (0.68 and 0.82) and $t_d$ (0.50 ms) of ARS-Mut were not much different from the values of the free ARS-Mut ((d) to (e) in FIG. 2). In addition, the scatter plot of the ARS-Mut with adenine showed a distribution very similar to the distribution of the free ARS-Mut ((f) in FIG. 2).

From this, it was confirmed that the significant increase in the dwell time observed in the ARS-adenine complex was based on the specific interaction of ARS and adenine, which could be detected using nanopore.

<1-4>. Confirmation of Characteristic Nanopore Events of Partially Folded ARS Intermediates Two types of characteristic current blockade events were observed from ARS-adenine complex.

Specifically, the free ARS showed only a type-I event with a single level of ion current blockade, but a duel-level electric signal was observed in the ARS-adenine complex through the mixture of the type I and type-II events ((a) in FIG. 3). The type-II event showed a characteristic pattern of two current levels (referred to as $I_{II1}$ and $I_{II2}$) with the distinctive duration ($t_{II1}$ and $t_{II2}$), which indicates that they occurred in the adenine bound ARS RNA. The average $I/I_0$ value of level 1 ($I_{II1}$) of the type-II event is 0.45, which corresponds to about 50% of level 2 ($I_{II2}$). After separating the types I and II nanopore events of the complex, each type of event was statistically analyzed. The type I and II events of the ARS-adenine complex is different in the average value and dwell time of $I/I_0$ ((b) to (c) in FIG. 3). In particular, the dwell time ($t_{II}$, 2.14 ms) of the type-II event was measured longer than that ($t_I$, 0.28 ms) of the type-I event, exhibited significant difference. In addition, the scatter plots of the type I and II events showed clearly distinguished distributions ((d) in FIG. 3).

From this, it can be seen that the interaction of riboswitch and ligand can be detected using a nanopore by using the characteristic current blockade event observed in the ARS-adenine complex.

<1-5>. Construction of ARS Structural Change Detection Model Using Nanopores

Based on the nanopore data analyzed in Examples 1-3 and 1-4, a molecular model was constructed for nanopore events of free riboswitch and ligand-bound riboswitch ((e) in FIG. 3).

Three molecular states (free ARS, intermediate and ARS-adenine complex) may be produced during the tertiary folding of the ARS RNA induced by adenine. It is known that the blunt end A type RNA duplex does not translocate the α-HL nanopore because of its large diameter of A-type duplex. Therefore, the free ARS generates frequent bumping signals with a short average dwell time (0.38 ms) and a single-level current blockade ((a) in FIG. 2). Similarly, the ARS-adenine complex with a P1 stem of the stable blunt end, which is the final product of the folding process, cannot enter the pore, so a type I bumping event with an average $t_I$ of 0.28 ms is occurred ((b) in FIG. 3).

Figure 6:
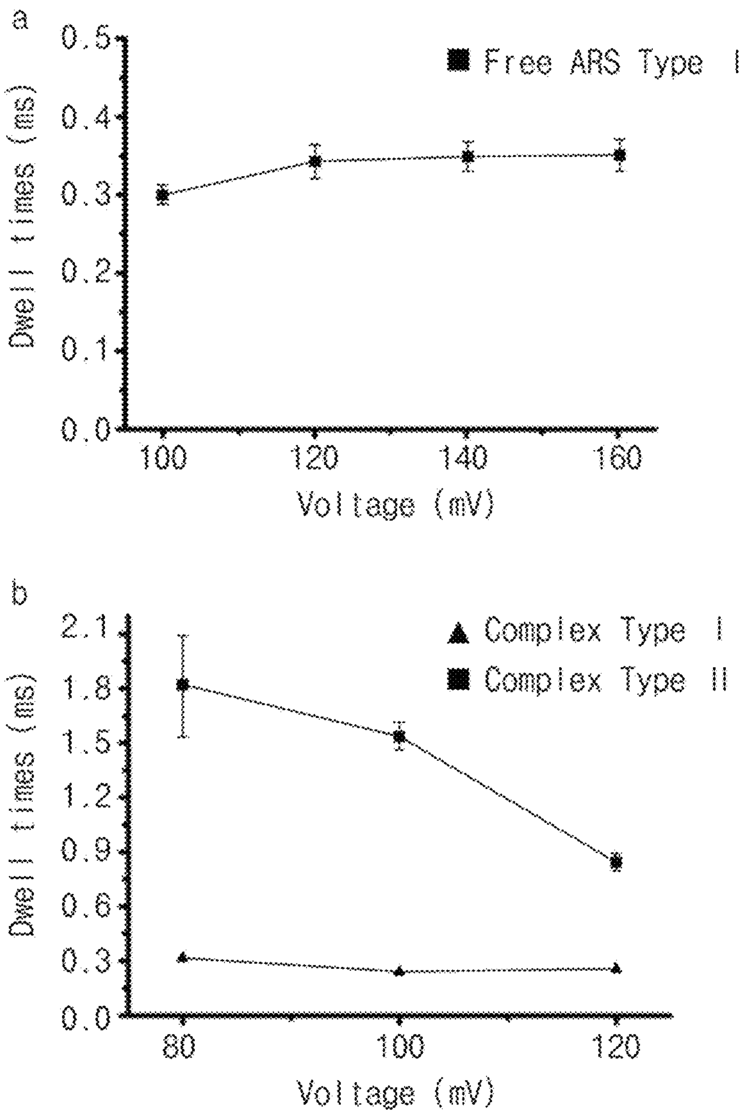
FIG. 6 shows a change in dwell time of the event as a voltage increases: (a) in FIG. 6 shows the dwell time according to the applied voltage (+100 mV, +120 mV, +140 mV and +160 mV) of type-I event of free ARS; (b) in FIG. 6 shows the dwell time according to the applied voltage (+80 mV, +100 mV and +120 mV) of the ARS-adenine complex. Here, the type I and type-II events are represented by triangles and squares, respectively, and an error bar represents a standard error.

Unlike the free ARS or the complex, partially folded ARS intermediate having a secondary structure of flexible end stems and matastable state can translocate nanopore through two steps. The first step is to capture the secondary structure of the adenine-bound ARS and unzip the structure in a single strand ((e) in FIG. 3). During the sub-dwell time $t_{II1}$, the spiral duplex of the adenine-bound ARS is unzipped outside the vestibule of the α-HL nanopore to unpair the base pairs. Once the unzipping of the ARS is completed, the translocation process of nanopore was performed in the second step. It is immediately released from the nanopore during the sub-dwell time $t_{II2}$ ((e) in FIG. 3, the middle column). It was confirmed that the type-II event was the result of the nanopore translocation through the voltage-dependent nanopore detection. The type-II event occurring in the complex showed a significant decrease in dwell time (from +80 mV to +120 mv) as the voltage increased (FIG. 6). This indicates that the analyte translocates the nanopore.

Unlike the type II nanopore translocation event, the type-I event of the free ARS and complex showed similar dwell time even if the voltage increased.

Taken together, the adenine-bound ARS generates the type II translocation signal with a two-stage ion current blockade and the dwell time 7.64 times longer (2.14 ms) than that of the type-I event. Such a significant time delay can be generated as a result of unzipping, that is, separation of duplexes into single strands of adenine-bound intermediates using flexible end stems.

From this, it can be seen that a single molecule-based nanopore sensor is a useful platform for detecting a temporary and partially folded intermediate generated in the ligand bound-coupled RNA folding path. Unlike the existing nanopore technology in which free state and complex structural changes are detected, it screens riboswitch bound drug through intermediate detection, which is different from the existing technology.

<1-6>. Confirmation of Possibility of Nanopore-Based Drug Screening

The interaction between riboswitch and ligand was detected by nanopore to confirm whether the drug can be screened. In addition, it was confirmed that the specific binding of riboswitch and ligand can be detected even when various ingredients of natural products are included.

Figure 4:
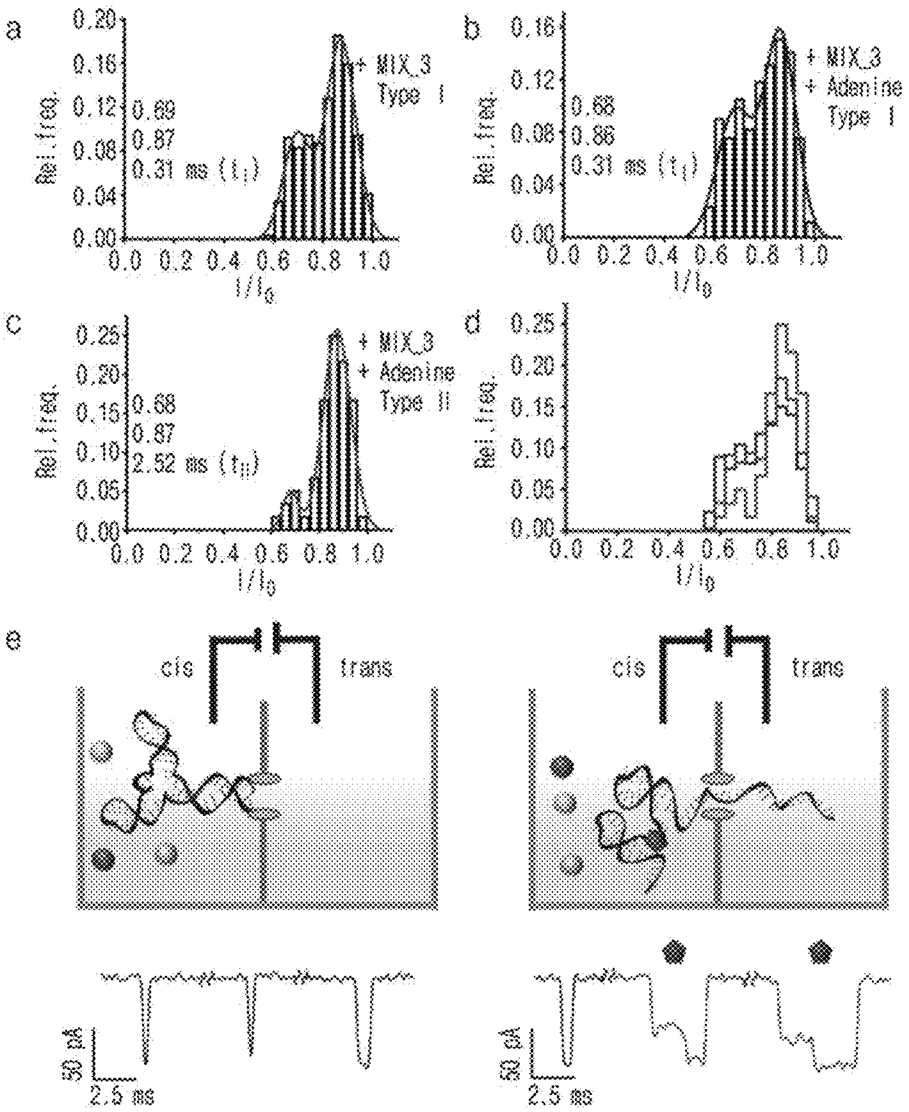
FIG. 4 shows a nanopore measurement result for specific interactions between ARS and adenine in the presence of multiple non-binding compounds: (a) in FIG. 4 shows an $I/I_0$ histogram with $t_I$ for the type-I event of ARS when a mixture of non-binding compounds is present without adenine; (b) in FIG. 4 shows an $I/I_0$ histogram with $t_I$ for the type-I event of ARS when the mixture of non-binding compounds is present with adenine; (c) in FIG. 4 is an $I/I_0$ histogram with $t_{II}$ for the type-II event of ARS in the presence of adenine and MIX-3; (d) in FIG. 4 shows a comparison of $I/I_0$ histograms of the type-I event and type-II event of ARS MIX-3 with only MIX-3 and ARS with adenine; (e) in FIG. 4 is a schematic model for nanopore translocation of specific interaction between ARS and adenine.
Figure 7:
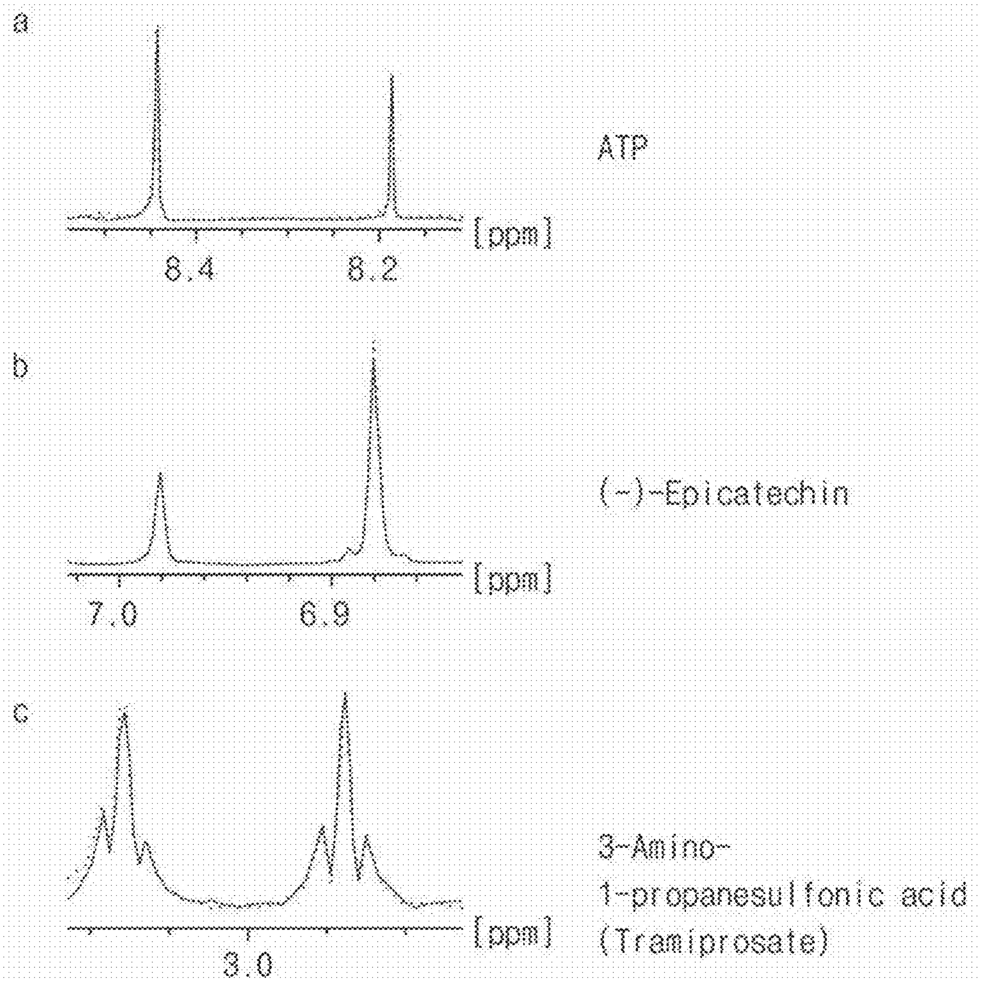
FIG. 7 shows 1D-CPMG analysis for the non-binder compounds: solid and dotted lines show the 1D CPMG spectrum of the compound in the absence and presence of ARS, respectively.

Specifically, a nanopore measurement was performed using a mixture of non-binding compounds (MIX-3: ATP, (−)-epicatechin and tramiprosate) that do not bind to ARS in the absence or presence of adenine (FIG. 4). The MIX-3 generated only the type-I event, and showed the average $I/I_0$ of 0.69 and 0.87 and the relatively short $t_d$ (0.31 ms). This means that MIX-3 binds to the ARS and does not induce three-dimensional structural changes ((a) in FIG. 4). In the MIX-3, the non-binding ability of each compound was further confirmed by 1D CPMG, a ligand observation NMR screening technique (FIG. 7)

However, if adenine is added to MIX-3, a mixture of the type I and type-II events was appeared, and the latter exhibited a nanopore dwell time ($t_{II}$, 2.52 ms) that was increased up to 6.6 times more than that of the free ARS ((c) in FIG. 4).

From this, it can be seen that the characteristic deep current blockade of the type-II event can be used to identify the binding of the drug to the ARS and to increase the dwell time. In addition, it can be seen that the specific binding of the adenine to the ARS can be detected by nanopores even in complex samples including several substances ((e) in FIG. 4)

<1-7>. Drug Screening Using ARS Structural Change Detection Model

Nanopore-based drug screening was performed using the structural change detection model of Example 1-5.

Specifically, in silico screening of an antibiotic agent for ARS was performed using the LibDock and CDOCKER programs in the Discovery Studio software. In a library consisting of 766 natural products, 40 natural products with the highest docking scores on the Libdock and CDOCKER calculations or the lowest interaction energy were first selected (Table 2).

TABLE 2

| Compound | LibDock score (kcal/mol) | Compound | CDOCKER Interaction energy (kcal/mol) |
|---|---|---|---|
| NC1 | 172.57 | NC21 | −54.58 |
| NC2 | 172.57 | NC22 | −38.16 |
| NC3 | 161.69 | NC23 | −36.87 |
| NC4 | 158.44 | NC24 | −35.56 |
| NC5 | 158.18 | NC25 | −29.35 |
| NC6 | 155.07 | NC26 | −28.95 |
| NC7 | 152.2 | NC27 | −28.18 |
| NC8 | 151.41 | NC28 | −25.3 |
| NC9 | 148.99 | NC29 | −25.01 |
| NC10 | 144.52 | NC30 | −23.55 |
| NC11 | 143.68 | NC31 | −23.51 |
| NC12 | 143.68 | NC32 | −22.77 |
| NC13 | 143.11 | NC33 | −22.76 |
| NC14 | 139.99 | NC34 | −22.02 |
| NC15 | 139.43 | NC35 | −21.23 |
| NC16 | 136.68 | NC36 | −21.04 |
| NC17 | 136.68 | NC37 | −20.41 |
| NC18 | 134.68 | NC38 | −20.41 |
| NC19 | 134.37 | NC39 | −20.18 |
| NC20 | 134.37 | NC40 | −19.66 |

Figure 8:
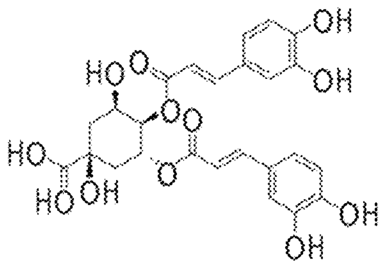
FIG. 8 shows the chemical structures of the ARS-targeting compounds developed through Experimental Example 6.
Figure 8:
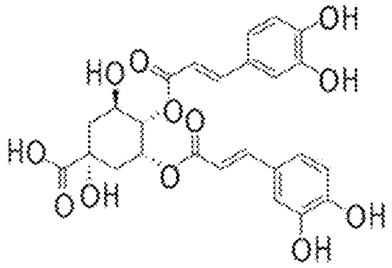
Figure 8:
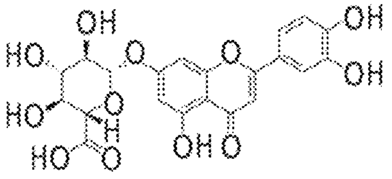

40 natural products were divided into 10 groups, each consisting of 4 natural products, and the nanopore-based drug screening was performed. In the nanopore screening results, three groups with more than 10% of the type II specific translocation event were selected. Subsequent nanopore-based screening for each selected individual compound finally discovered three new ARS targeting-natural products (FIG. 8). The hit compounds of NCI (3,4-dicaffeoylquinic acid), NC2 (4,5-dicaffeoylquinic acid), and NC4 (luteolin-7-glucuronide) all exhibited types II translocation event and dwell time of 4.1 to 7.3 times greater than that of free ARS ((a) to (d) in FIG. 5). In order to identify whether heat natural products bind to the ARS, 1D CPMG test was performed with three hit compounds in the absence or presence of the ARS using the NMR spectroscopy.

Figure 5:
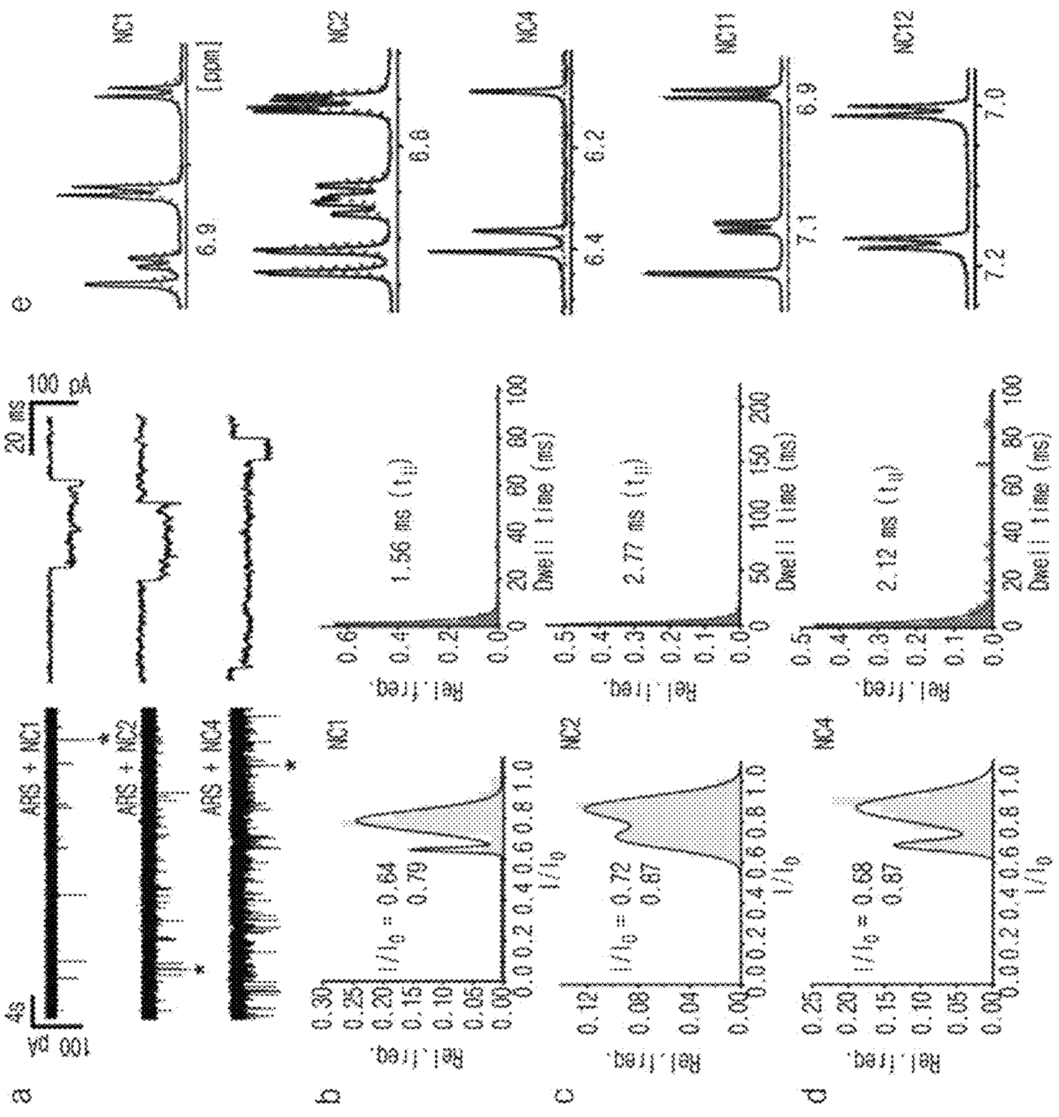
FIG. 5 shows a nanopore-based drug screening approach for ARS RNA: (a) in FIG. 5 shows a current trace of a nanopore event for ARS when there are hit compounds (NC1, NC2 and NC4) in which representative type-II events (marked with an asterisk) detected at ARS along with hit compounds are shown in the right column; (b) to (d) in FIG. 5 show histograms of $I/I_0$ and dwelling time $t_{II}$ for the type-II event of the ARS generated in binding to each hit compound (NC1 (b), NC2 (c) and NC4 (d)); (e) in FIG. 5 shows the analysis result of 1D CPMG NMR of hit compounds and ARS non-binding compounds (NC11 and NC12) in the presence of ARS presence in which a solid line and a dotted line show the 1D CPMG spectrum of natural substances in the absence and presence of ARS, respectively.

Unlike the natural materials (NC11 and NC12) that do not bind to the ARS, the definite binding of the ARS to the hit natural products was confirmed with dramatic peak line-broadening and/or significant chemical shift change in ID CPMG spectrum after adding the ARS to NC1, NC2 and NC4 ((e) in FIG. 5). In particular, it was confirmed that NC1 and NC2 shared common scaffolds for new antibiotic drugs, and all three hit compounds were derived from herbs with antibacterial activity or anti-inflammatory activity: *Lonicera japonica* (NC1 and NC2) and *Marchantia berteroana* (NC4).

From this, the nanopore-based drug screening technology of the disclosure can be expanded and applied to various RNA targets associated with diseases, and it can be seen that the natural product containing a plurality of components can be screened in a short time with high efficiency without pre-classification in a single component.

Example 2

Class II RNA Target: Riboswitch Target with Short P1 Stem

<2-1>. Preparation of TRS RNA

TPP riboswitch (thiamine pyrophosphate-sensing riboswitch or thi-box riboswitch, TRS) is a factor that regulates gene expression through various mechanisms in bacteria, archaea, fungi, and plants by directly binding to thiamine pyrophosphate(TPP). TRS regulates genes involved in the synthesis or translocation of thiamine and its phosphorylated derivatives. TRS consists of five helical stems (P1 to P5), two hairpin loops (L3 and L5) and three binding sites (J2/4, J3/2 and J4/5).

TRS RNA was synthesized by Integrated DNA Technologies (Coralville, IA, USA), and sequence information was shown in Table 3 below. TRS RNA was dialyzed against 10 mM potassium phosphate (pH 6.2), 50 mM KCl buffer for more than 12 hours. TRS RNA was annealed by heating at 95° C. for 5 minutes and then slowly cooling at room temperature. All nanopore experiments were performed at 500 nM concentration.

TABLE 3

| Name | Sequences (5'→3') | Length | SEQ ID NO |
|---|---|---|---|
| TRS | GCGACU CGGGG UGCCC UUCUG CGUGA AGGCU GAGAA AUACC CGUAU CACCU GAUCU GGAUA AUGCC AGCGU AGGGA AGUCGC | 82 nt | 3 |

<2-2>. Construction of TRS Structural Change Detection Model

The α-hemolysin nanopore was used to confirm the interaction of free TRS and ligands at a single molecule level.

Specifically, in the buffer containing 10 mM potassium phosphate (pH 6.2), 2 mM $MgCl_2$ and 1M KCl, 500 mM free TRS was added to the cis face of a lipid bilayer with α-HL nanopore. When applying (+) voltage on the nanopore, it was observed that the TRS was driven by electrophoresis to block the ion current. As a result of statistically analyzing the nanopore event of the free TRS, on average, the dwell time in the pores was measured to be 0.28 ms (b in FIG. 11).

Two types of characteristic current blockade events were observed in the free TRS. In the free TRS, a mixture of the type-I event with single-level ion current blockade and the type-II event with dual-level ion current blockade was observed. This is a phenomenon in which since the free TRS has the relatively short base pairs of P1 stem, 6 pairs, an end is unstable in aqueous solution. In the case of the electrical signal that appears in the free TRS, the average value of the dwell time in the nanopore of type-I event was measured at 0.26 ms, and the average value of the dwell time of type-II event was 3.39 ms, which is relatively long compared to that of the type-I event. ((c) in FIG. 11 and (a) in FIG. 12).

Figure 9:
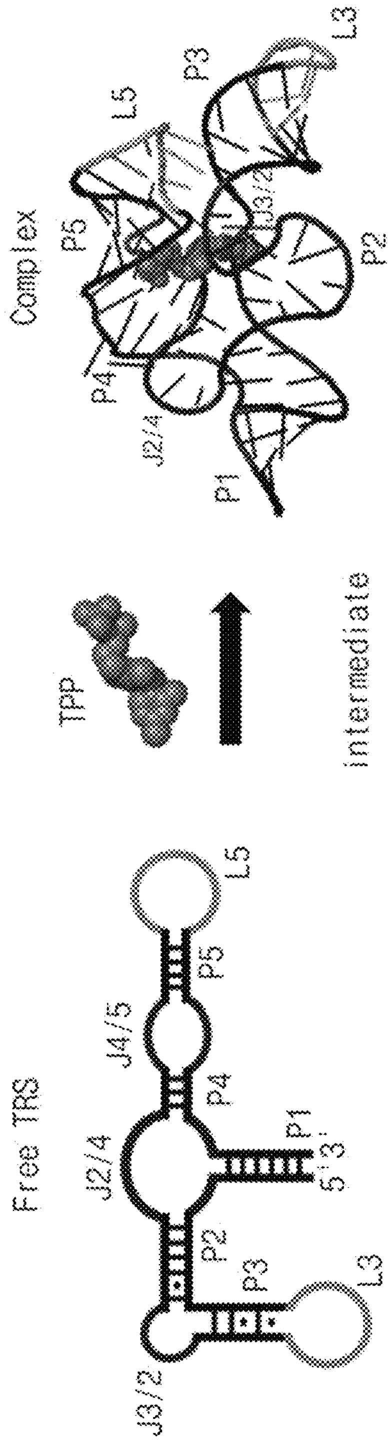
FIG. 9 shows a tertiary folding of TPP riboswitch (TRS) induced by TPP ligand binding.

The TRS causes a three-dimensional structural change (ligand-dependent folding) as the TPP ligands bind to the TRS, and the pyrimidine portion of the TPP forms an intercalation pocket with the P2 and P3 spiral stems, and the other spiral stems P4 and P5 provide a water-lined binding with the pyrophosphate portion of the pyrophosphate. Thus, the TRS-TPP complex structure compared to the free TRS structure has a compact and rigid folding structure. Three-dimensional structural changes by the binding of the TPP ligand of the TRS form a final TRS-TPP complex through intermediate state structure. This transient intermediate state structure can be observed by the nanopore-based analysis. A significant change was found between the nanopore signals in the structure of the free TRS and the intermediate state prior to the formation of the TRS-TPP complex (FIG. 9).

Figure 10:
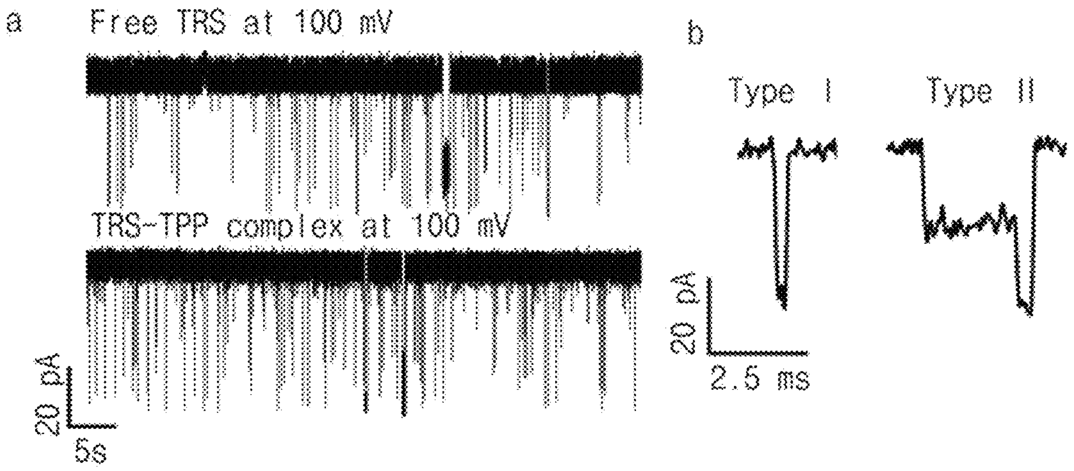
FIG. 10 shows nanopore events of free TRS and TRS-TPP complex: (a) shows current trace records for free TRS and TRS-TPP complex; (b) shows two types of nanopore events.

Specifically, the TRS-TPP complex was added to the cis face of the lipid bilayer with the α-HL nanopore. When applying (+) voltage on the nanopore, as the TRS-TPP complex enters the pores by electrophoresis, the ionic current is blocked. In the current blockade event of the TRS-TPP complex, both type-I and type-II events were observed and active nanopore current traces were confirmed (FIG. 10). In the statistical analysis of the nanopore event of the TRS-TPP complex, the average dwell time was 0.22 ms, which was measured similarly to the average dwell time of the entire nanopore events in the free TRS ((b) in FIG. 11). The dwell times for the type-I and type-II events observed in the TRS-TPP complex were measured at 0.21 ms and 4.37 ms, respectively, ((c) in FIG. 11 and (a) in FIG. 12).

Figure 11:
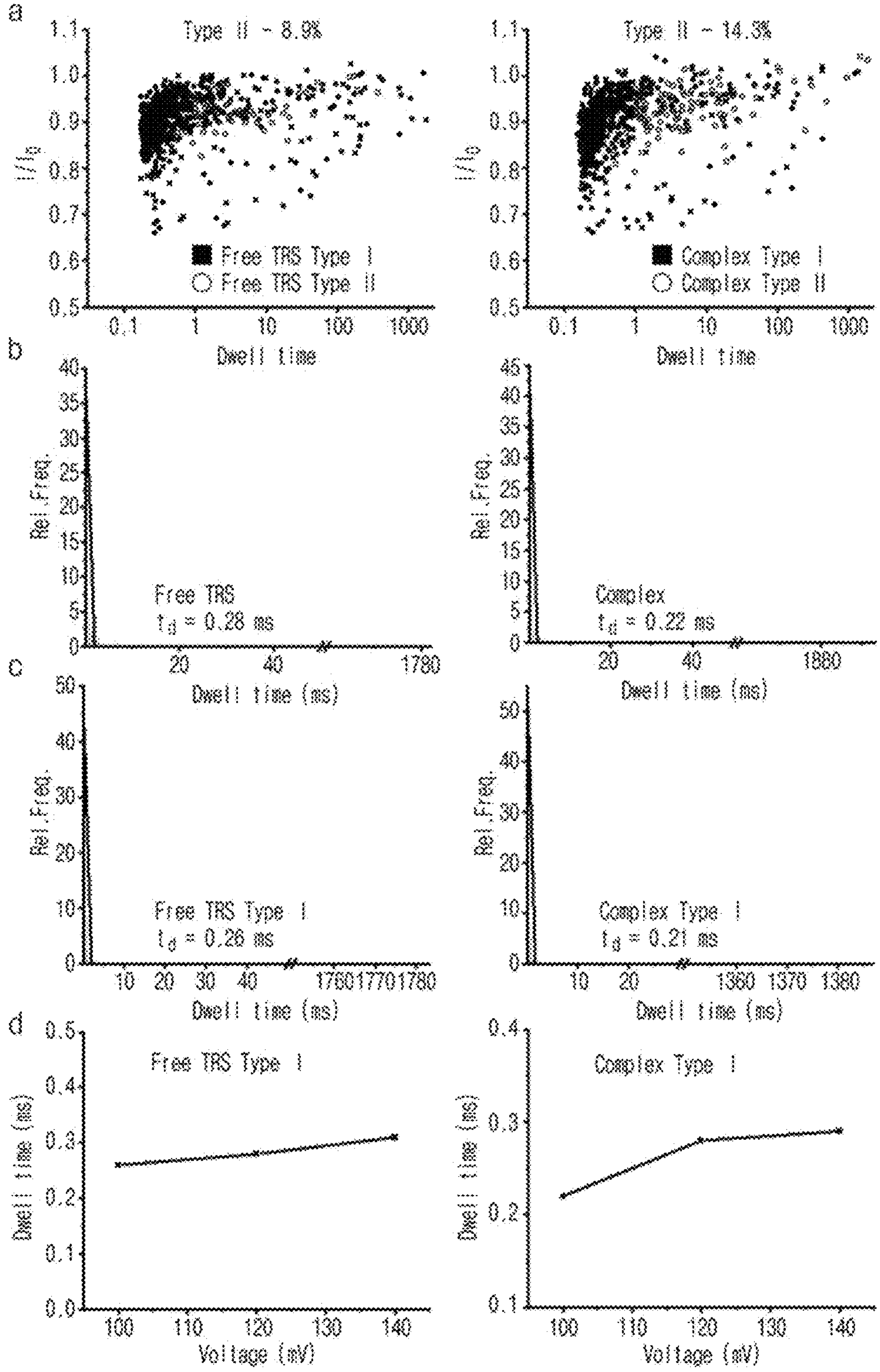
FIG. 11 shows statistical analysis results for nanopore events of free TRS and TRS-TPP complex: (a) shows scatter plots of type-I event and type-II event for free TRS and TRS-TPP complex; (b) shows dwell time histograms of total events for free TRS and TRS-TPP complex; (c) shows dwell time histograms of type-I events for free TRS and complex; (d) shows a voltage dependence of dwell time at the type-I event of free TRS and TRS-TPP complex at the applied potential of 100 to 140 mV, whereby it was confirmed that the dwell time of type-I event is almost identical or increased as the applied potential increases.
Figure 12:
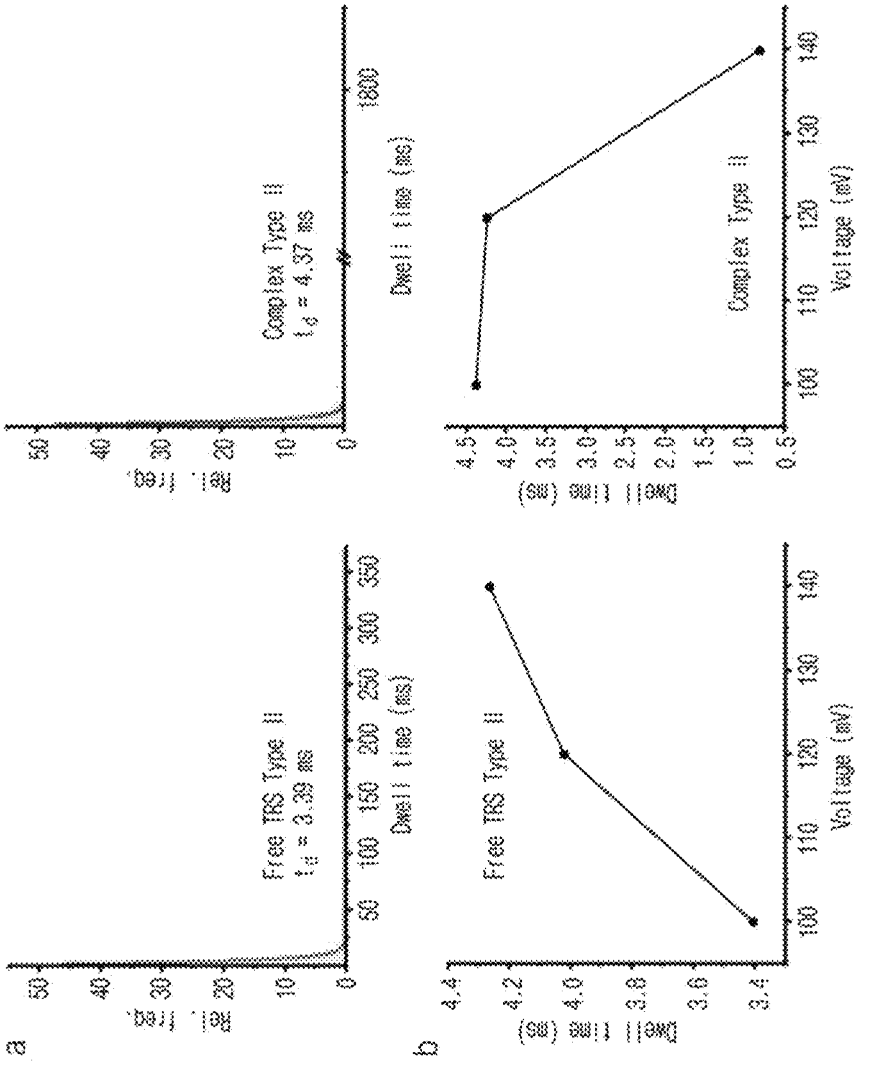
FIG. 12 shows statistical analysis results for the type-II event of free TRS and TRS-TPP complex: (a) shows a histogram of dwell time of type-II event; (b) shows a voltage dependence of dwell time at the type-II event of free TRS and TRS-TPP complex at the applied potential of 100 to 140 mV, whereby it was confirmed that the dwell time of type-II event is reduced as the applied potential increases.

In the two types of specific current blockade events in the free TRS, the dwell time was found to increase as the applied voltage increases (from +100 mV to +140 mV) through voltage-dependent nanopore detection ((d) in FIG. 11 and (b) in FIG. 12). This indicates that the analyst cannot translocate the nanopore and generates a bumping signal. In addition, the rate of Type-II event in the free TRS accounted for 8.9% of the total events ((a) in FIG. 11).

In the case of the type-I event of the TRS-TPP complex, it was confirmed through the voltage-dependent nanopore detection that as the applied voltage increased (from +100 mv to +140 MV), the analyst could not translocate the nanopore because of increased dwell time and the bumping signals were generated. However, in the type-II event, the nanopore dwell time tended to decrease as the voltage increased, so that it was confirmed that the type-II event of the TRS-TPP complex translocated the nanopore.

Three molecular states (free TRS, intermediate and TRS-TPP complex) may be produced during the tertiary folding of the TRS induced by the TPP. The free TRS with blunt end does not translocate the α-HL nanopore and generates frequent bump signals with short average dwell time (0.26 ms) and single-level current blockade. In addition, the TRS has a short P1 stem consisting of six base pairs, which is relatively short, and thus has flexible end in the acceptance liquid. As a result, the P1 stem is unzipped in the vestibule of the α-HL nanopore, but eventually does not translocate the nanopore and generates a bumped duel-level current blockade. The TRS-TPP complex with a stabilized structure and a P1 stem, which is the final product of the folding process, cannot enter the pore, so that the type-I bumping event of the average dwell time of 0.21 ms is generated.

Unlike the free TRS or the TRS-TPP complex, TRS/TPP binding intermediate, which mostly has unstable structures, can translocate the nanopore through two steps. The first step is to capture the secondary structure of the TPP bound TRS and unzip the structure in a single strand. Once the unzipping of the spiral structure of the TPP bound TRS is completed, the translocation process of the nanopore was performed in the second step. As a result, the TRS intermediate formed by the binding of TPP generates the type-II dual-level current blockade event. It was confirmed that the type-II event rate generated by the intermediate was 14.3%, which is significantly increased compared to that in the free TRS (FIG. 11). In the case of the type-II event generated by the intermediate formed upon the binding of TPP, it was confirmed that the dwell time was increased by 1.3 times compared to that of the type-II event shown in the free TRS, and the event rate also increased by 1.6 times (FIGS. 11 and 12).

From this, it can be seen that a single molecule-based nanopore sensor is a useful platform for detecting a temporary and partially folded intermediate generated in the TPP ligand-induced RNA folding path.

In summary of the molecular mechanism, since the free TRS has the blunt end structure based on nanopore measurement data, the free TRS cannot translocate the nanopore and generates the bumping signal. However, since the P1 stem has a relatively short base pairs, six base pairs, the end portion is flexible so that it may enter the vestibule of the α-HL nanopores, but it cannot be completely unzipped by the S stems of P2, P3, P4 and P5, so that the type-II event is observed.

Similarly, the TRS-TPP complex to which the TPP is bound also completes the tertiary folding to form the blunt end structure, and the base pairs are further stabilized, so that the complex cannot translocate the nanopore and generates the bumping type-I signal. However, the intermediate structure, which is an intermediate product generated when the folding is caused by the binding of the TPP to the TRS, shows a unique type-II nanopore signal due to the structural flexibility of RNA.

In this way, by confirming the specific signal of the TRS-TPP complex through the nanopore measurement, the target substance for the bacterial-derived riboswitch can be screened and used to treat the diseases regulated by the riboswitch. In particular, it can be applied as a useful development for discovering an antibacterial agent or an antibiotic agent.

Example 3

Class III RNA Target: RNA with Hairpin Structure

<3-1>. Preparation of RNA-Targeting Molecules with Hairpin Structure

Novel RNA targets, 5'L-iav-RNA and 3'L-iav-RNA, were synthesized by Integrated DNA Technologies (Coralville, IA, USA) by designing and RNA leader sequences at the 5' end or 3' end using a promoter sequence conserved in the influenza A virus RNA among the RNAs with a hairpin structure. Two RNA samples were dialyzed against the buffer containing 10 mM potassium phosphate (PH 6.2) and 50 mM KCl for more than 12 hours. The RNA samples were annealed by heating at 95° C. for 5 minutes and then slowly cooling at room temperature.

TABLE 4

| Category | Sequences (5'→3') | Type of nucleic acid | SEQ ID NO |
|---|---|---|---|
| 5'L-iav-RNA | $(A)_{24}$AGUAGAAACAAGGCUUCGGCCUGCUUUUGCU | ribo | SEQ ID NO 4 |
| 3'L-iav-RNA | AGUAGAAACAAGGCUUCGGCCUGCUUUUGCU$(AC)_{12}$ | ribo | SEQ ID NO 5 |

<3-2>. Construction of 5'L-iav-RNA Structural Change Detection Model

The α-hemolysin(α-HL) nanopore was used to confirm the interaction of RNAs with hairpin structure and ligands at a single molecule level.

The structures of 5'L-iav-RNA having a hairpin structure and 6,7-dimethoxy-2-(1-piperazinyl)-4-quinazolinamine (DPQ), which is a target drug for 5'L-iav-RNA, were shown ((a) in FIG. 13).

Specifically, in the buffer containing 10 mM phosphate (pH 6.2) and 1M KCl, 500 mM 5'L-iav-RNA was added to the cis compartment of a lipid bilayer with a single α-HL nanopore. When applying (+) 100 mV voltage on the nanopore, the 5'L-iav-RNA and the complex are driven by electrophoresis to block the ion flow ((b) in FIG. 13).

First, as a result of statistically analyzing the nanopore event in the free 5'L-iav-RNA, the average current blockade intensity (ΔI) of the nanopore event was measured at 76.9 pA, and the average dwell time was measured at 0.58 ms ((c) in FIG. 13).

It is known that 6,7-dimethoxy-2-(1-piperazinyl)-4-quinazolinamine(DPQ), a target drug for 5'L-iav-RNA, is bound to the internal loop portion of the influenza RNA to stabilize the hair pin structure of the RNA (*Chem commun* (2014), 50 (3), 368-370). When a stable interaction between 5'L-iav-RNA and DPQ ligand was detected using the nanopore, a significant change in the nanopore current trace was confirmed between the free 5'L-iav-RNA and the 5'L-iav-RNA-DPQ complex ((b) in FIG. 13).

In addition, as a result of statistical analysis of nanopore events of the complex according to the binding rate of DPQ ligand, in the complex having a ratio of 1:50, the average current blockade (ΔI) of the nanopore event was measured at 78.6 pA and the average nanopore dwell time was measured at 1.14 ms. In the complex having a ratio of 1:100, the average current blockade of 75 pA and the dwell time of 1.47 ms were measured. Finally, it was observed that the time for 5'L-iav-RNA to translocate the protein nanopore was significantly increased as the concentration of the free 5'L-iav-RNA and DPQ ligand is increased at ratios of 1:50 and 1:100 ((c) in FIG. 13).

Neomycin, another target ligand of influenza A virus RNA, is known to stabilize the hairpin structure, a two-dimensional structure of the RNA, by binding to the phosphate backbone of the influenza A virus RNA with an internal loop. When statistical analysis was conducted for the nanopore event of the 5'L-iav-RNA-neomycin complex, the average dwell time of the nanopore event was significantly increased from 0.43 ms to 3.48 ms (about 8.1 times) (FIG. 14).

In conclusion, after entering the vestibule of α-HL nanopore by adding 24 nucleotide leader sequences to the 5' end of the influenza A virus RNA with a blunt end, the two-dimensional hairpin structure of the RNA is designed so that unzipping can easily occur in the vestibule of the pore. Due to the binding of the target ligand, the two-dimensional hairpin structure of 5'L-iav-RNA is stabilized, and the process of unzipping base pairs in the vestibule of the nanopore occurs slowly, increasing the nanopore dwell time of the target ligand-bound RNA complex.

From this, it can be seen that a single molecule-based nanopore sensor is a useful platform for detecting the hairpin structure of the RNA stabilized by binding of ligand.

<3-3>. Construction of 3'L-iav-RNA Structural Change Detection Model

An RNA target (3'L-iav-RNA) was prepared by designing and adding a 24 nucleotide leader sequences to the 3' end so that free IAV RNA translocates the nanopore more efficiently compared to 5'L-iav-RNA.

Here, in order to remove factors that hinder RNA from translocating the nanopore due to partial folding of the poly$(A)_{24}$ leader sequences, the leader sequences of 3'L-iav-RNA was prepared by using poly$(AC)_{12}$ nucleotides.

Specifically, in the buffer containing 10 mM phosphate (pH 6.2) and 1M KCl, 500 mM 3'L-iav-RNA was added to the cis compartment of a lipid bilayer with a single α-HL nanopore. When applying (+) 100 mV voltage on the nanopore, the 3'L-iav-RNA and the complex are driven by electrophoresis to block the ion flow ((c) in FIG. 15). The average nanopore dwell time (7.30 ms) of the free 3'L-iav-RNA was significantly increased compared to the average nanopore dwell time (0.58 ms) of the free 5'L-iav-RNA. In the nanopore detection of the free 5'L-iav-RNA, partial folding of the poly$(A)_{24}$ leader sequences hinders translocation of the nanopore, so that a bumping event was occurred without translocation of some nanopores, and thus, the average dwell time was relatively short.

Example 4

Class IV RNA Target: RNA with Pseudoknot Structure

<4-1> Preparation of PreQ1-Sensing Riboswitch

PreQ1-sensing riboswitch(PreQ1 rs) is a factor that regulates gene expression in transcription or translation level by binding to nucleotide 7-aminomethyl-7-deazaguanine (PreQ1) directly to change the RNA sequences in bacteria. Bacteria with PreQ1 rs include *Bacillus antracis, Enterococcus* sp., and *Listeria monocytogenes*, which can cause serious diseases such as anthrax, cardiovascular dysfunction, food poisoning, and sepsis. The PreQ1 rs is a cis-acting element that regulates the expression of the genes involved in the biosynthesis of the nucleoside queuosin from the GTP, and controls the mRNA expression of the queC protein that is involved in queuosin biosynthesis in response to metabolite level. The PreQ1 rs acts as a feedback sensor for the concentration level of the PreQ1 and is involved in the survival of bacteria.

Figure 16:
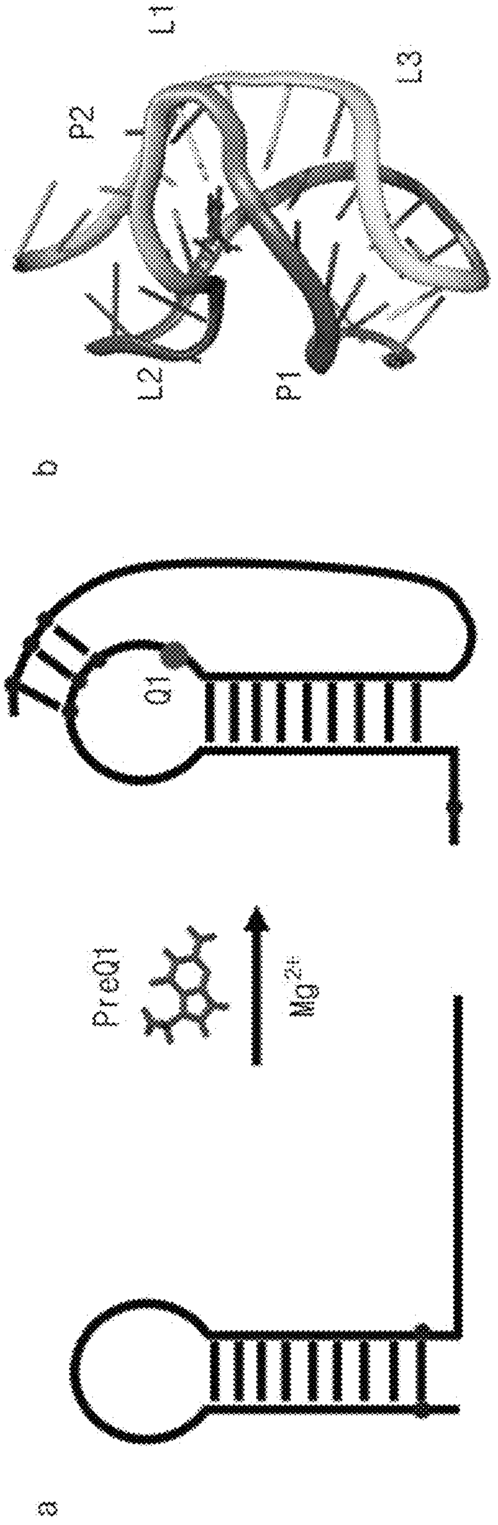
In FIG. 16, (a) shows a secondary structural change of riboswitch induced by preQ1-sensing riboswitch and preQ1, and (b) shows the tertiary folding of preQ1 and preQ1-sensing riboswitch complex (complex PDB code: 2L1V).

The PreQ1 rs is a riboswitch having a hairpin structure in which the end of the A-high content (A-rich) sequences are conserved. When a ligand binds to the stem portion of the hairpin structure, the A-rich sequences interact with the hairpin structure to form two or more stem-loops entangled with each other, and the stems form a pseudoknot structure, a structure that looks like a single double helix (FIG. 16).

The PreQ1 rs is synthesized by Integrated DNA Technologies (Coralville, IA, USA). The PreQ1 rs used in the test was designed by adding GG sequences to the 5' end of the 34nt basic aptamer sequences for the ease of secondary verification (NMR analysis, etc.) of the riboswitch structural change by binding of the PreQ1 ligand. The sequence information is shown in Table 5 below. The PreQ1 rs RNAs were dialyzed against 10 mM potassium phosphate (pH 6.2) buffer for at least 12 hours. After heating RNAs at 95° C. for 5 minutes, it was cooled quickly in the ice and annealed. All nanopore tests were performed at 500 nM concentration.

TABLE 5

| Name | Sequences (5'→3') | Length | SEQ ID NO |
|---|---|---|---|
| PreQ1 rs | GGAGAGGUUCUAGCUACACCCUCUAUAAAAA ACUAA | 36 nt | 6 |

After forming the complex with DPQ ligand and 3'L-iav-RNA in a ratio of 1:50, the complex was added to the cis compartment of the lipid bilayer with the α-HL nanopore. In the statistical analysis of nanopore events, it was confirmed that the nanopore average dwell time was significantly increased to 9.52 ms ((b) in FIG. 15). In addition, the increased dwell time of 3'L-iav-RNA by DPQ binding was also confirmed in the nanopore current trace ((c) in FIG. 15). It was confirmed that DPQ binding effectively stabilizes the two-dimensional hairpin structure of influenza A virus RNA, thereby delaying the process of unzipping base pairs in the vestibule of the nanopore.

Figure 15:
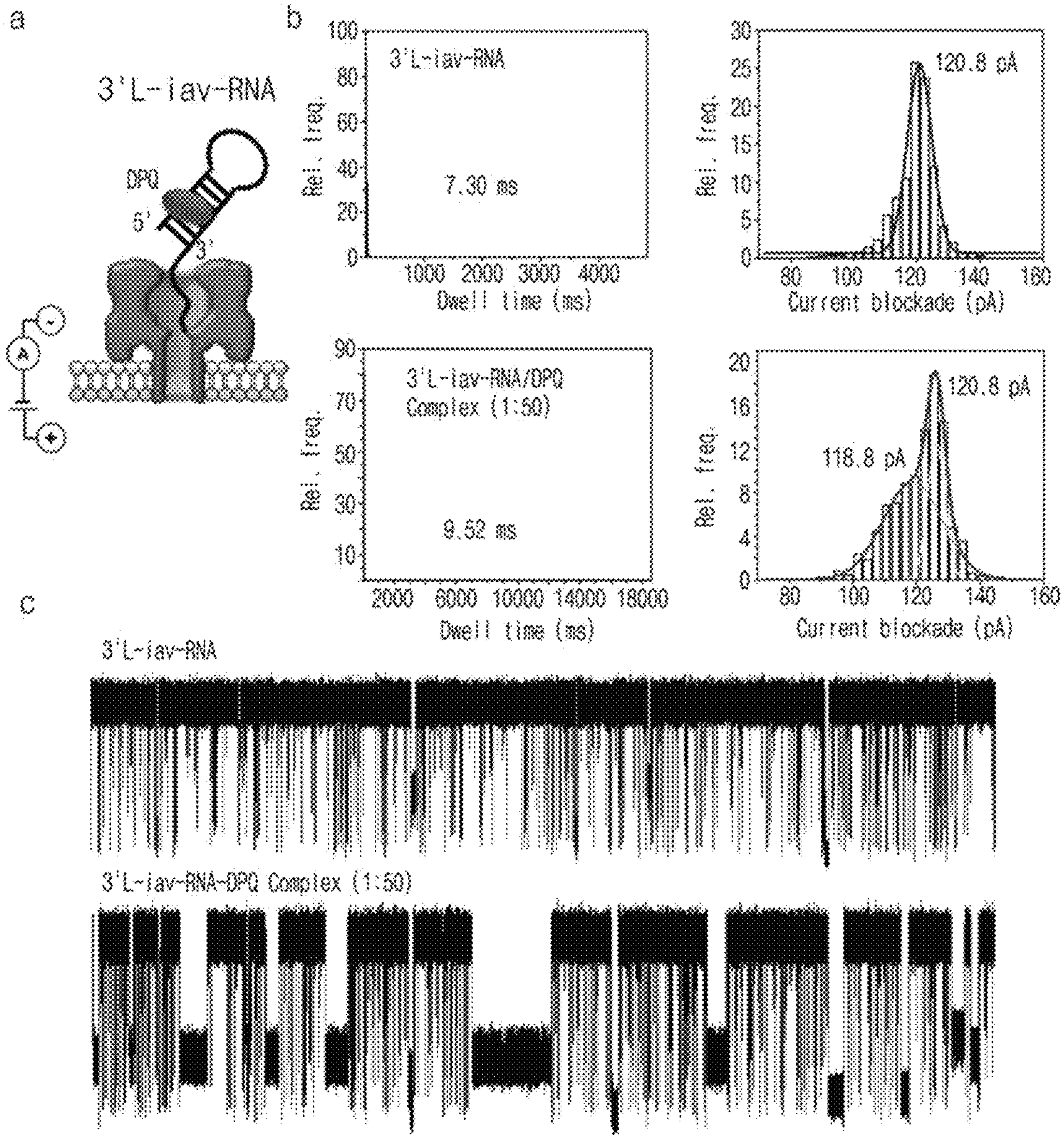
FIG. 15 shows a detection method of nanopore-based RNA-drug complex for IAV RNA using 3'L-iav-RNA: (a) shows a structural model of 3'L-iav-RNA/DPQ probe complex, (b) shows a histogram of dwell time and current blockade for free 3'L-iav-RNA and 3'L-iav-RNA/DPQ complex (molar ratio of 1 to 50), (c) shows nanopore raw data at the applied voltage of +140 mV.

It can be seen that the events with significantly increased nanopore dwell time due to ligand binding are easy to read, and from this, influenza A virus RNA having a hairpin structure can be detected with only 1 minute nanopore data. Accordingly, it can be seen that rapid diagnosis is possible (FIG. 15)

<4-2> Construction of PreQ1-Sensing Riboswitch Structural Change Detection Model The α-hemolysin nanopore was used to confirm the interaction of free PreQ1 rs and ligands at a single molecule level.

The PreQ1 rs is known as the smallest aptamer domain in nature with the size of 34 nucleotides. The PreQ1 rs with the hairpin structure, in which the A-rich end is conserved, causes a three-dimensional structural change (ligand-dependent folding) as the PreQ1 ligand binds to the stem portion, which causes the binding of the A-rich end and the base of the loop of the hairpin structure, thereby forming H-type pseudoknot structure (FIG. 16). This three-dimensional structural change can be observed in nanopore-based analysis.

Specifically, in the buffer containing 10 mM potassium phosphate (pH 6.2) and 1M KCl, 500 nM of free PreQ1 rs was added to the cis face of a lipid bilayer with the α-HL nanopore. It was observed that the PreQ1 rs was driven by electrophoresis to block the ion current if the (+) voltage was applied on the nanopore. As a result of statistically analyzing the nanopore events of the free PreQ1 rs, specific translocation events, type A and type B, were observed in addition to the bumping event in which the RNA target does not translocate the nanopore (FIG. 17, upper panel).

The type A and type B events are long-lived translocation events that occur specifically in nanopore-based detection of PreQ1 rs. The type A event is characterized in that current intensity at the start point of the event is low, current blockades at the start point and end point of the event are very different from each other, and multi-level current changes are dynamically repeated. The type B event is characterized in that the current blockades are almost the same at the start and end points of the event, and the current change occurs relatively less frequently (once or twice) than in the type A event. In the type A event, the current blockade was small at the start point of the event as the single-stranded RNA portion at the end that has already been unwound was first inserted into the pore, and then the stem-loop structure was unzipped, resulting in multiple current blockades. Accordingly, it was confirmed that at the end point of the event, as RNAs translocated the narrow constriction of the pore, the current blockade increased.

Since then, to confirm whether the interaction of ligands can be detected at a single molecule level, the PreQ1 rs-PreQ1 complex was added to the cis face of the lipid bilayer with the nanopore in the buffer containing 10 mm phosphate (pH 6.2) and 1M KCl. When the (+) voltage is applied to the nanopore, the ion current is blocked as the PreQ1 rs-PreQ1 complex enters the nanopore by electrophoresis. In the current blockade event of the PreQ1 rs-PreQ1 complex, both type A and type B events were observed, and active nanopore current traces were confirmed (FIG. 17, bottom panel).

Specifically, it was confirmed that the type A event, which occurs as the unzipped single-stranded RNA portion was first inserted into the nanopore, was higher in the free PreQ1 rs than in the PreQ1 rs-PreQ1 complex. On the other hand, in the type B event, the entire ligand-bound riboswitch was inserted into the nanopore rather than the single-stranded RNA, resulting in a higher current blockade from the start point of the event. Further, after a slight change in current occurred during unzipping, the ligand-bound riboswitch translocated with a similarly large current intensity at the end point of the event. The PreQ1 rs-PreQ1 complex has a stable structure than that of the free PreQ1 rs. Thus, it was observed that as the unzipping time increased, it was observed that the total dwell time of type B events increased significantly compared to type A events (FIG. 17).

As a result of comparing the frequency of multiple-level current signal compared to a single-level current signal that occurred within the unit time, in the free PreQ1 rs, the type A event rate was 70.2%, which was higher than the 29.8% of the type B event rate. However, in the PreQ1 rs-PreQ1 complex, the type A event rate was 26.5% and the type B event rate was 73.5%. Thus, the clear pattern change was confirmed that the type B event rate increased by about 1.5 times in the ligand-bound state (FIG. 18). From the above results, by confirming the change in the rate between specific signals in the PreQ1 rs-PreQ1 complex, which is different from the free PreQ1 rs riboswitch, through the nanopore measurement, it is possible to screen target substances for bacterial-derived riboswitch, and it can be seen that it is applicable to the treatment of diseases controlled by riboswitch, especially the development of antibacterial or antibiotics agents.

What is claimed is:

1. A method for screening an RNA-targeting drug, comprising:

detecting the presence of multi-level current signals and/or a change in dwell time of those signals associated with unzipping and translocation of a target RNA through a nanopore both before and after treating the target RNA with a candidate substance expected to bind to the target RNA; and selecting the candidate substance as a drug to be bound to the target RNA when there is a change in the presence of the multi-level current signals and/or the change in the dwell time of those signals.

2. The method of claim 1, wherein in the detecting step, three-dimensional structural change of the target RNA induced by binding of the candidate substance to the target RNA detected as the presence of the multi-level current signals and/or the change in the dwell time of those signals.

3. The method of claim 2, wherein the three-dimensional structural change of the target RNA delays the dwell time of the multi-level current signals associated with unzipping and translocation of the target RNA through the nanopore.

4. The method of claim 1, wherein the change in the presence of the multi-level current signals refers to an appearance of the multi-level current signals following treatment of the candidate substance, and the change in the dwell time of the multi-level current signals refers to a delay in the dwell time following the treatment of the candidate substance.

5. The method of claim 1, wherein the target RNA itself forms at least one stem-loop or a triplex structure.

6. The method of claim 5, wherein the target RNA comprises bacterial riboswitch or viral RNA promoter.

7. The method of claim 6, wherein the bacterial riboswitch is any one selected from the group consisting of purine riboswitch, lysine riboswitch, cyclic diGMP riboswitch, glmS riboswitch, TPP riboswitch, and FMN riboswitch.

8. The method of claim 1, wherein a protein that generates the nanopore is any one selected from the group consisting of a-hemolysin, ClyA, aerolysin, lysenin, CsgG, FhuA, FraC, MspA, PlyAB, Phi29, PA63, and OmpG.

9. The method of claim 1, wherein the RNA-targeting drug is an anticancer agent, a metabolic disease treatment, a degenerative disease treatment, a cardiovascular disease treatment, a lung disease treatment, an immune disease treatment, an antibacterial agent, an antibiotics, or an antiviral agent.

* * * * *